(12) United States Patent
Kriesel et al.

(10) Patent No.: US 6,391,006 B1
(45) Date of Patent: May 21, 2002

(54) FLUID DELIVERY APPARATUS WITH RESERVOIR FILL ASSEMBLY

(75) Inventors: Marshall S Kriesel, St. Paul; Steven M. Arnold, Minnetanka; James Garrison, Minneapolis; Farhad Kazemzadeh, Bloomington; Thomas N Thompson, Richfield, all of MN (US)

(73) Assignee: Science Incorporated, Bloomington, MN (US)

(*) Notice: Subject to any disclaimer, the term of this patent is extended or adjusted under 35 U.S.C. 154(b) by 0 days.

(21) Appl. No.: 09/562,740

(22) Filed: May 1, 2000

Related U.S. Application Data

(63) Continuation-in-part of application No. 09/250,036, filed on Feb. 12, 1999, now Pat. No. 6,086,561, which is a continuation-in-part of application No. 09/017,047, filed on Feb. 2, 1998, now Pat. No. 5,962,794, which is a continuation-in-part of application No. 08/718,686, filed on Sep. 24, 1996, now Pat. No. 5,721,382, which is a continuation-in-part of application No. 08/432,220, filed on May 1, 1995, now abandoned.

(51) Int. Cl.[7] .............................................. A61M 37/00
(52) U.S. Cl. ....................... 604/132; 604/153; 604/191
(58) Field of Search .............................. 604/85, 86, 82, 604/131, 132, 133, 151, 153, 156, 185, 191, 184, 890.1

Primary Examiner—Anhtuan T. Nguyen
(74) Attorney, Agent, or Firm—James E. Brunton, Esq.

(57) ABSTRACT

An elastomeric bladder stored energy type infusion apparatus that can be filled with a medicinal fluid and, after being filled, can efficiently delivery the medicinal fluid to the patient at a selected rate. The apparatus includes a delivery component for delivering medicinal fluid to the patient and a fill component that can expeditiously be used to fill the fluid reservoir of the delivery component in the field.

26 Claims, 20 Drawing Sheets

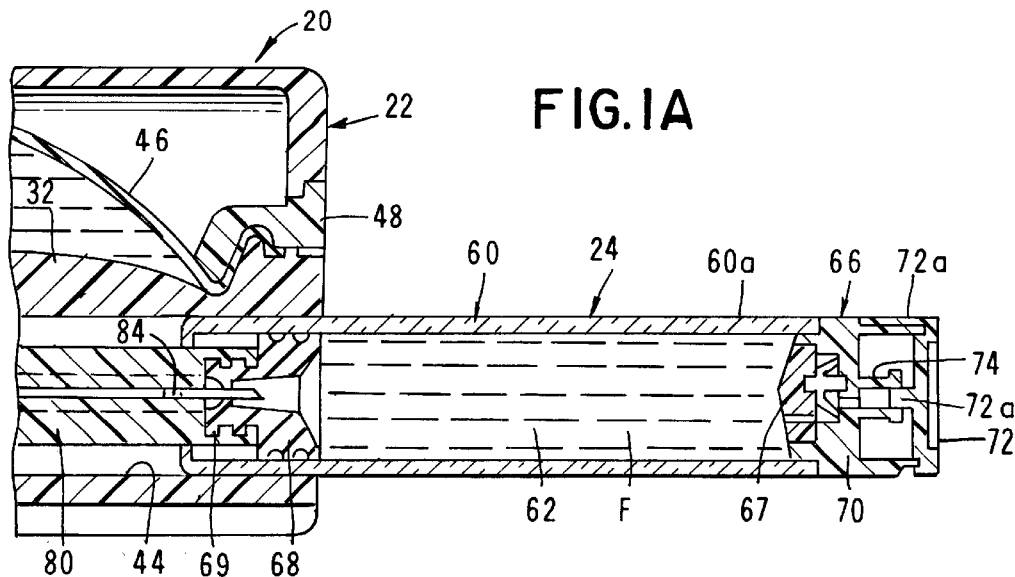
FIG.1A
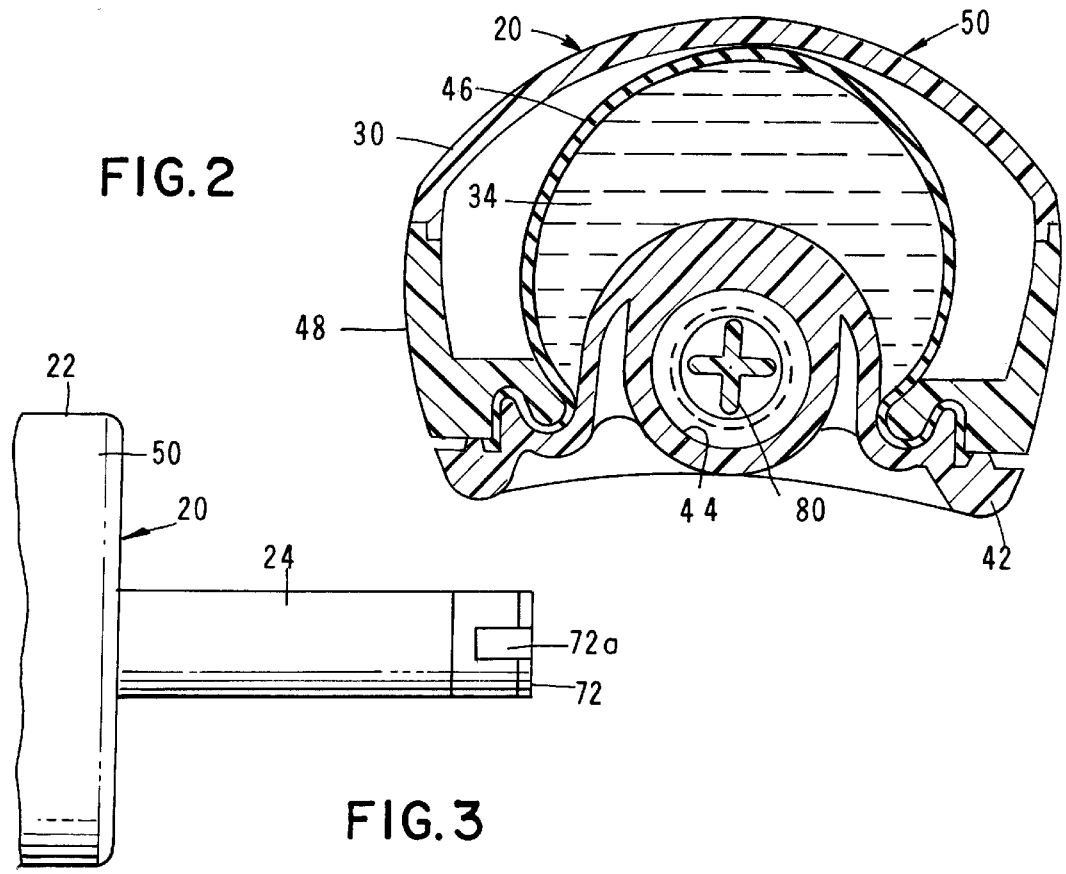
FIG.2
FIG.3

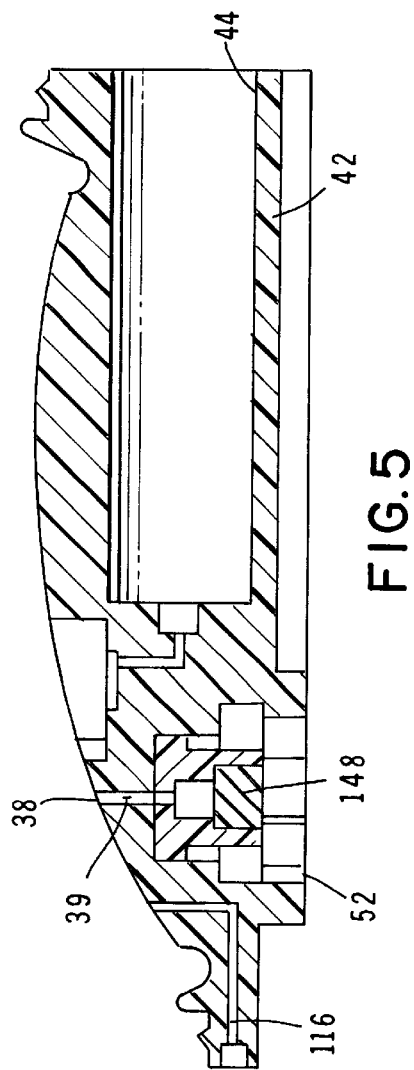
FIG. 5A
FIG. 5B
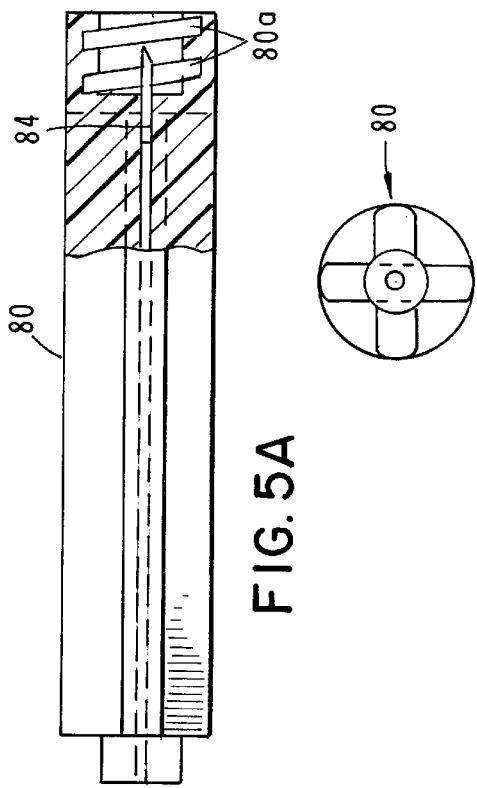
FIG. 5
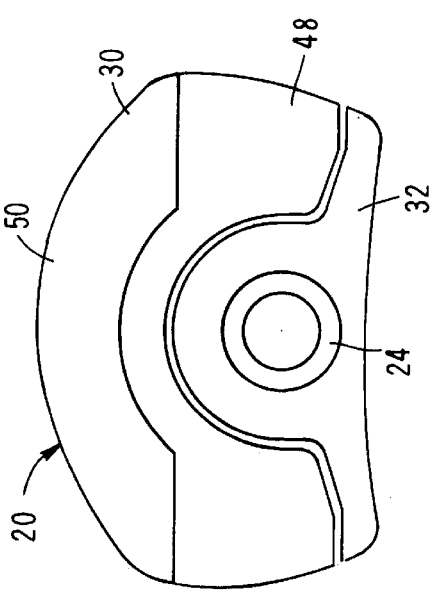
FIG. 4

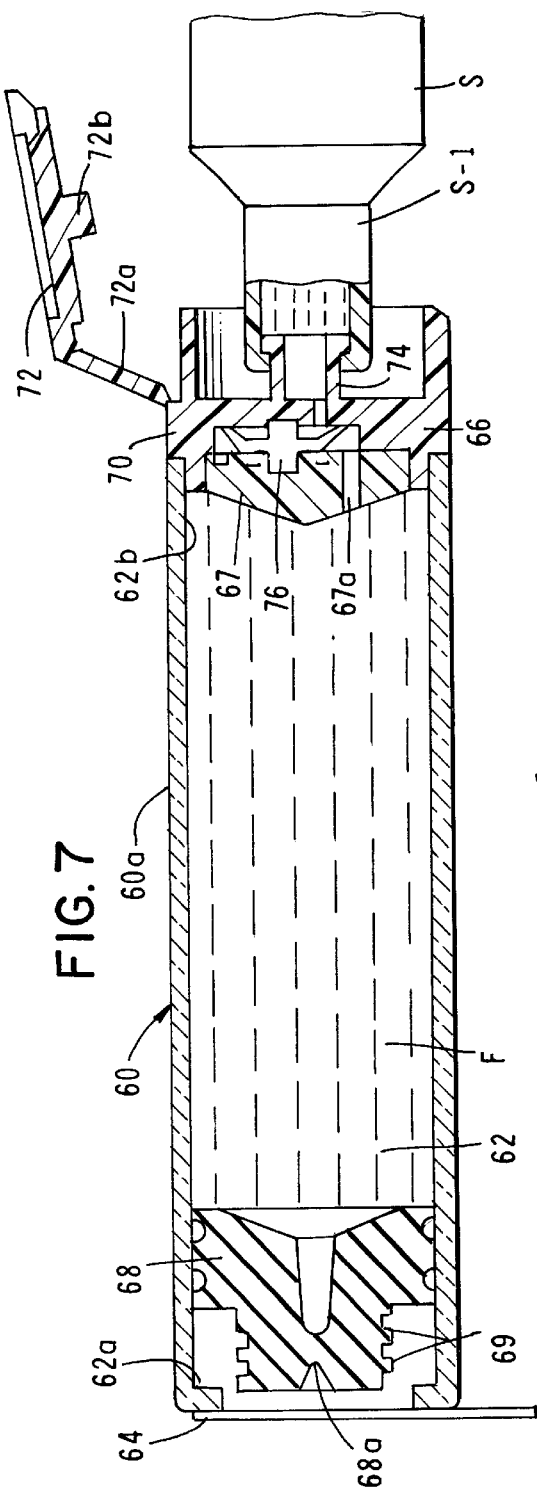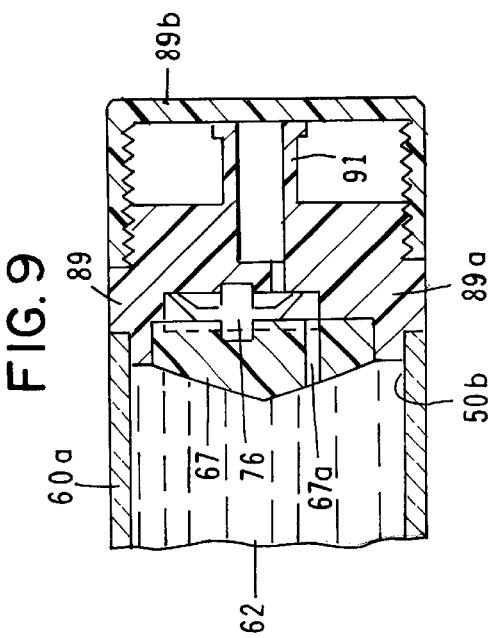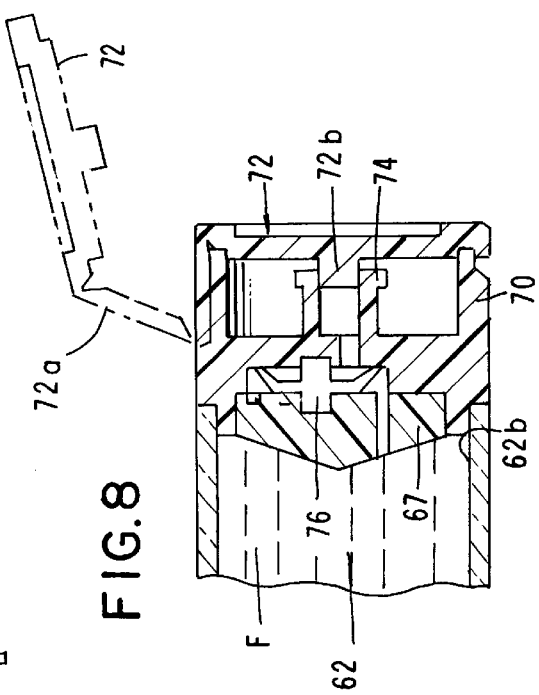

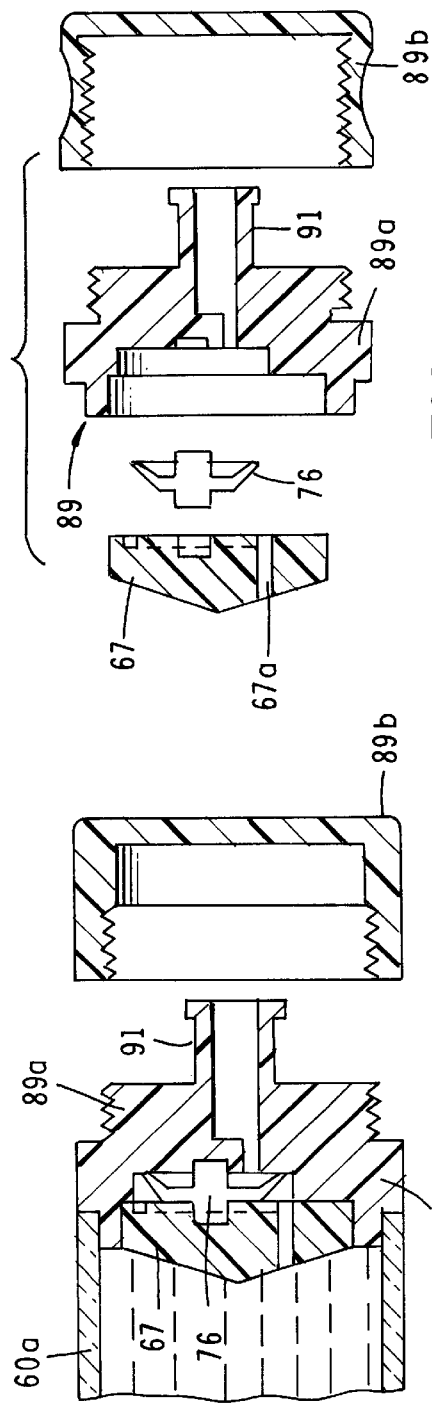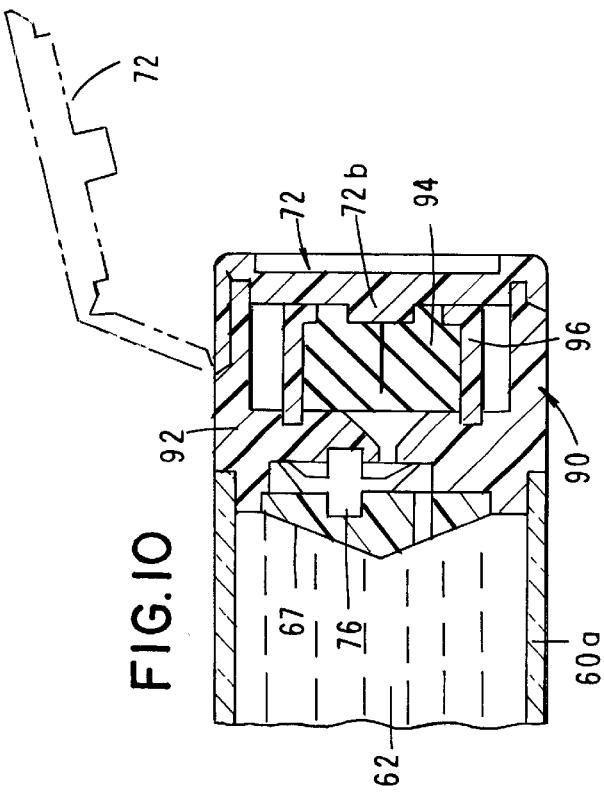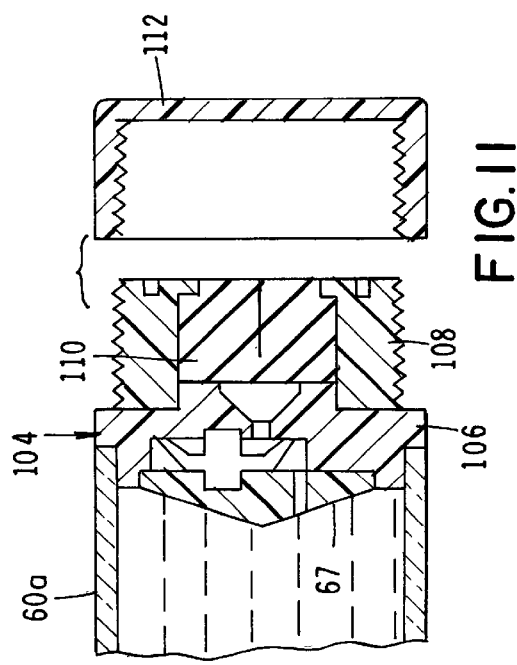

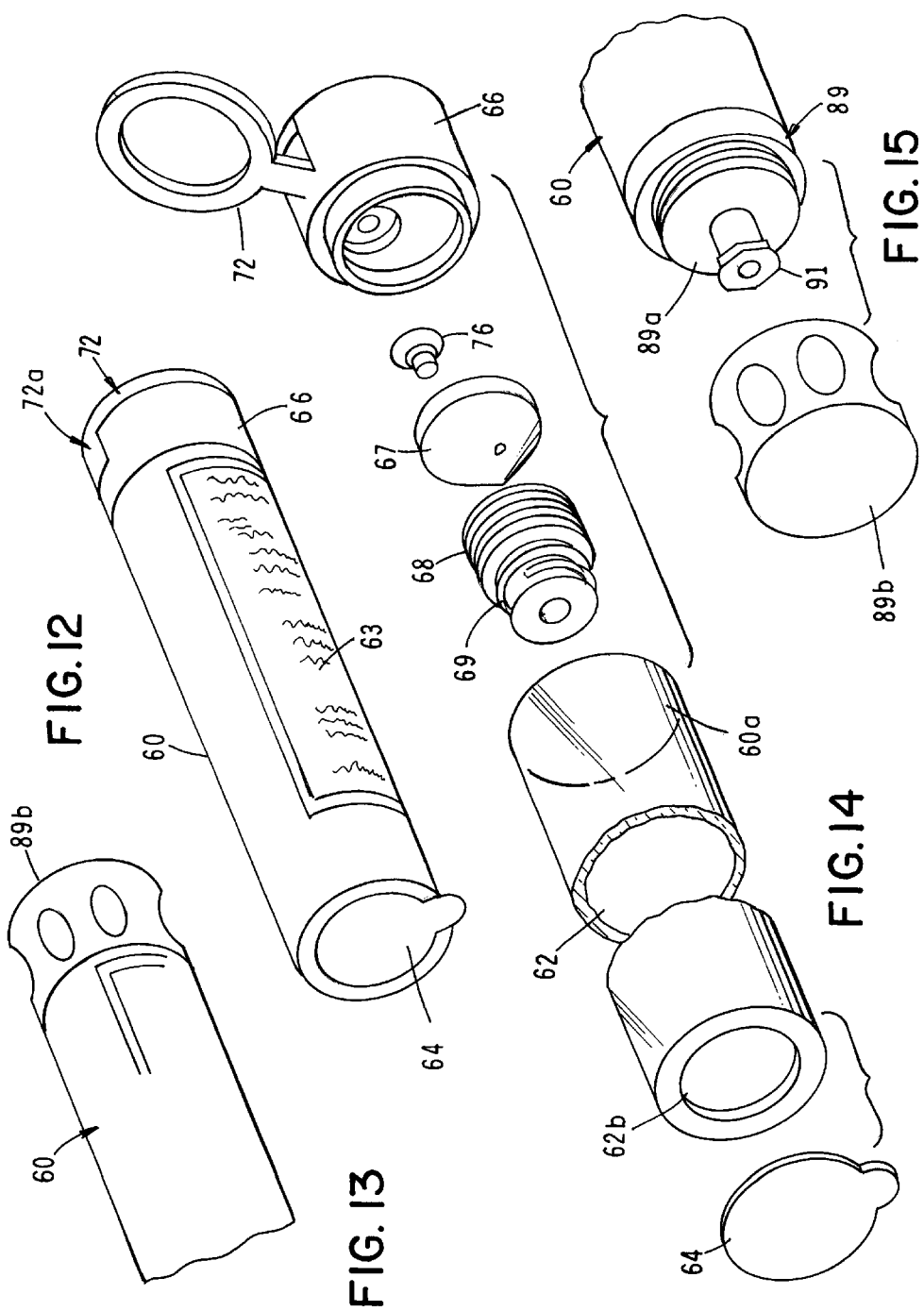

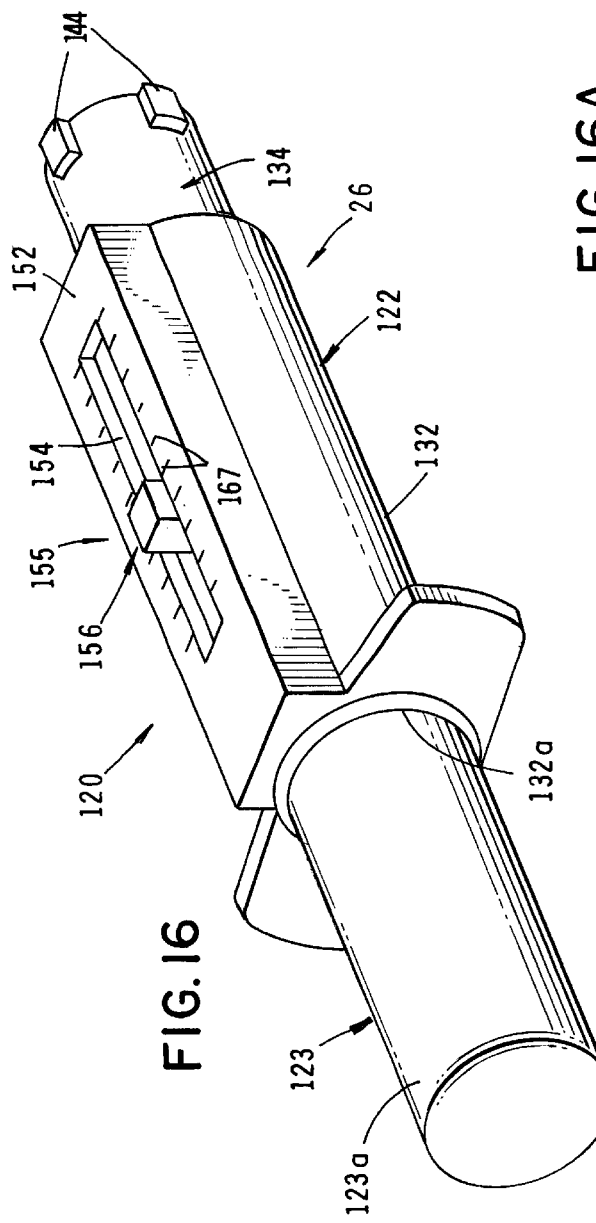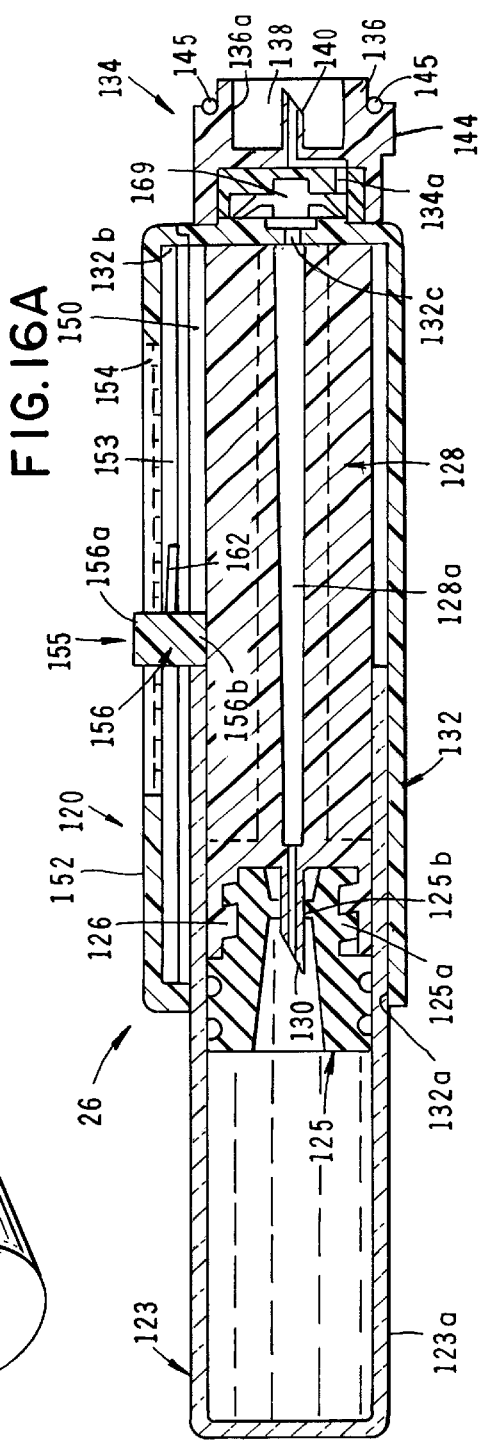

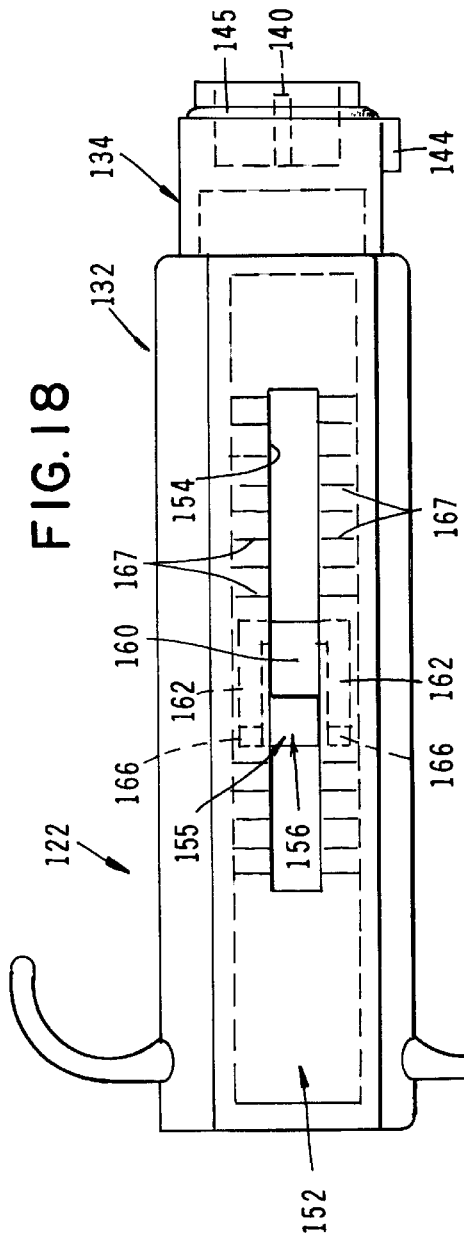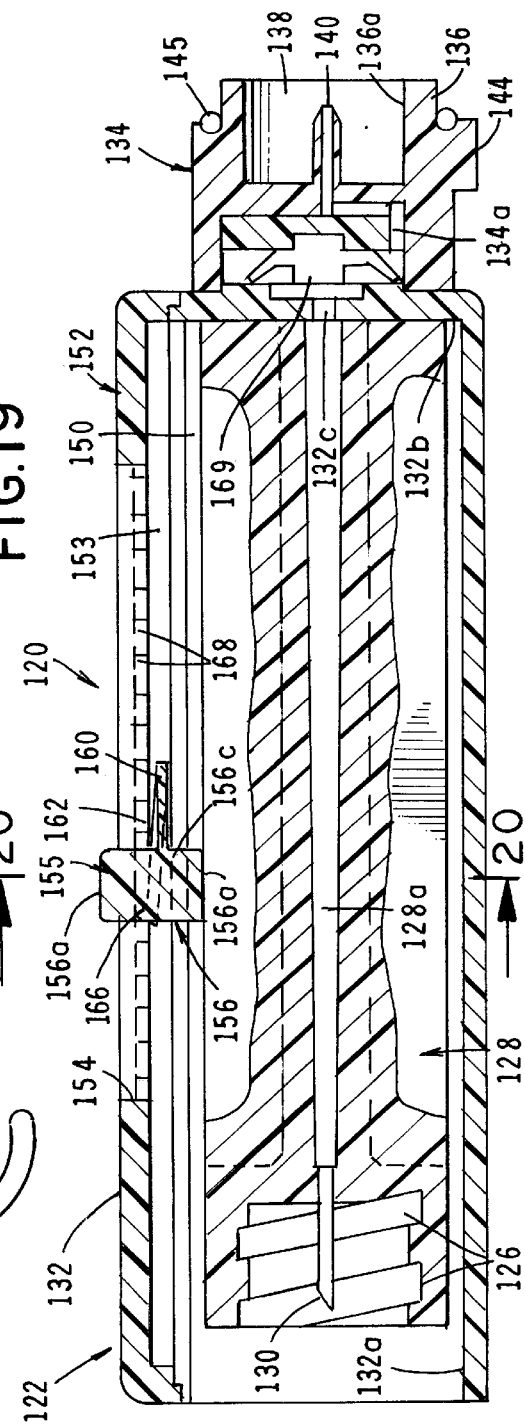

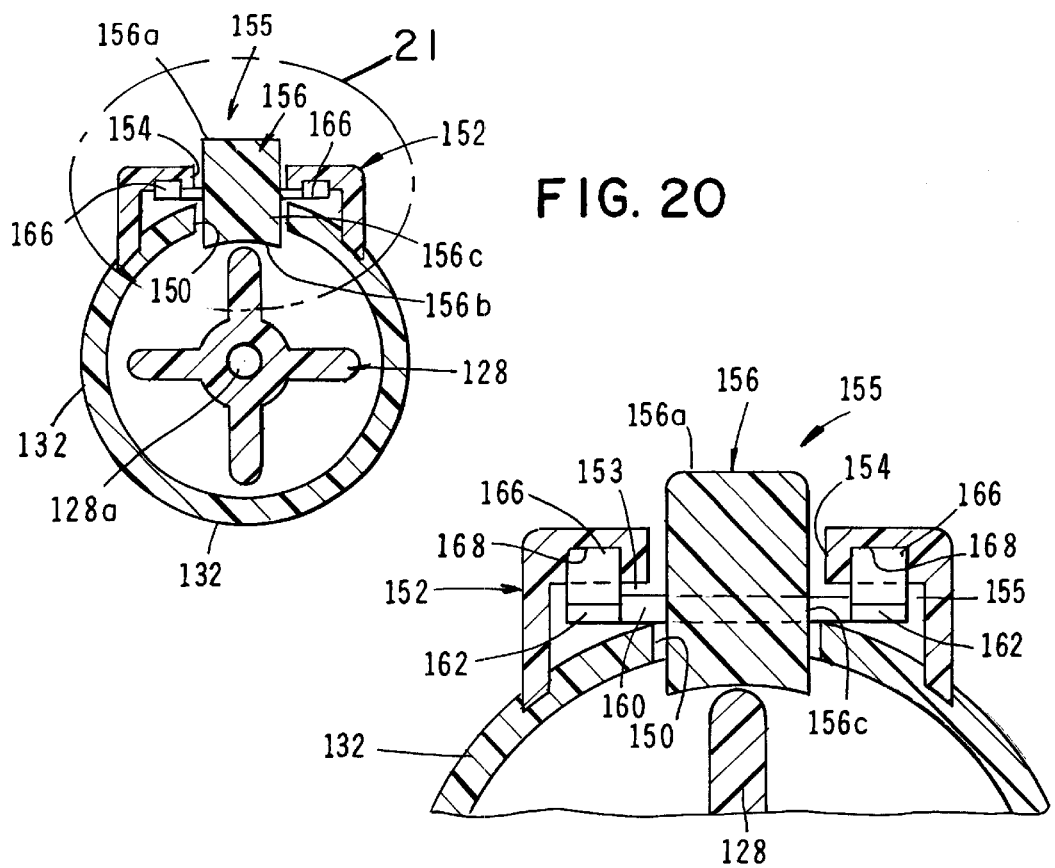
FIG. 20
FIG. 21
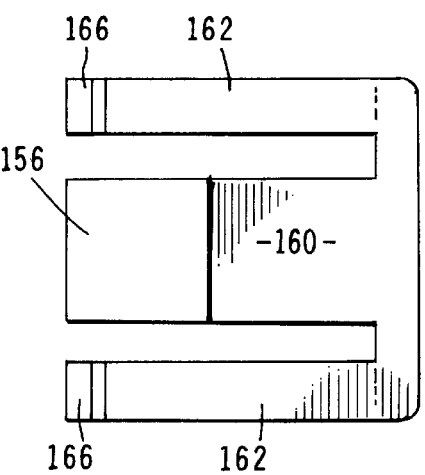
FIG. 22
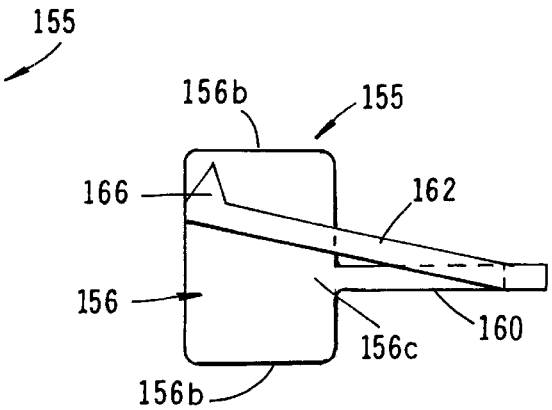
FIG. 23

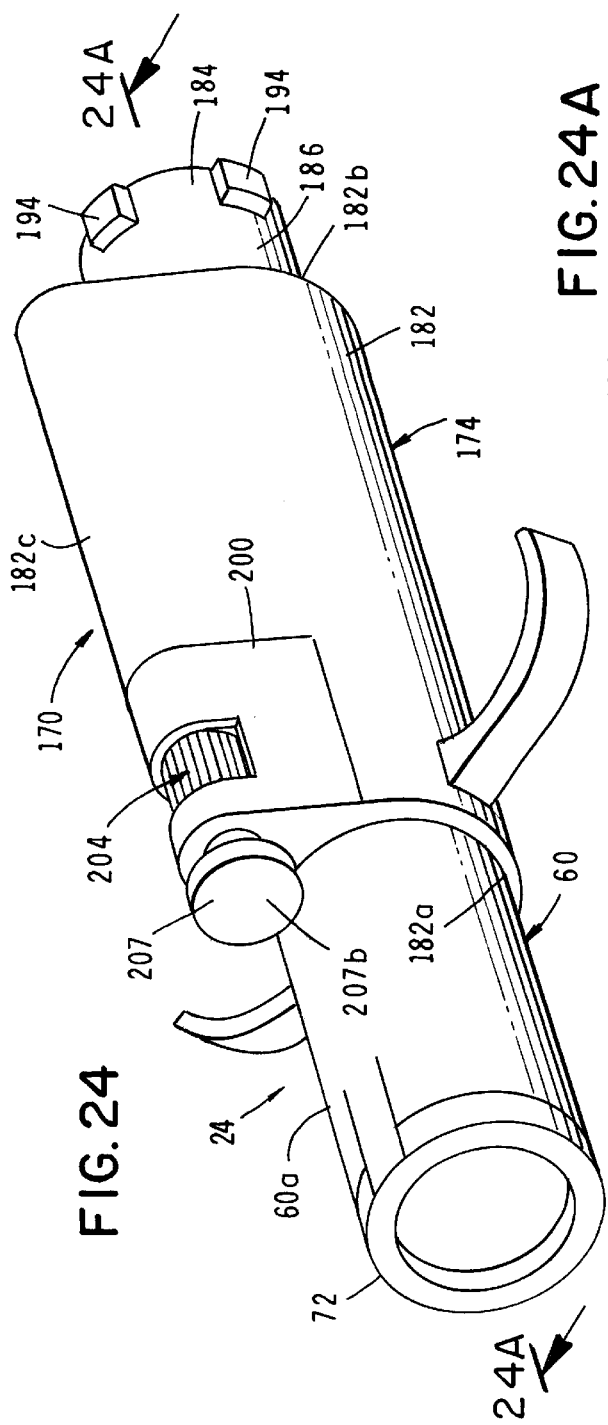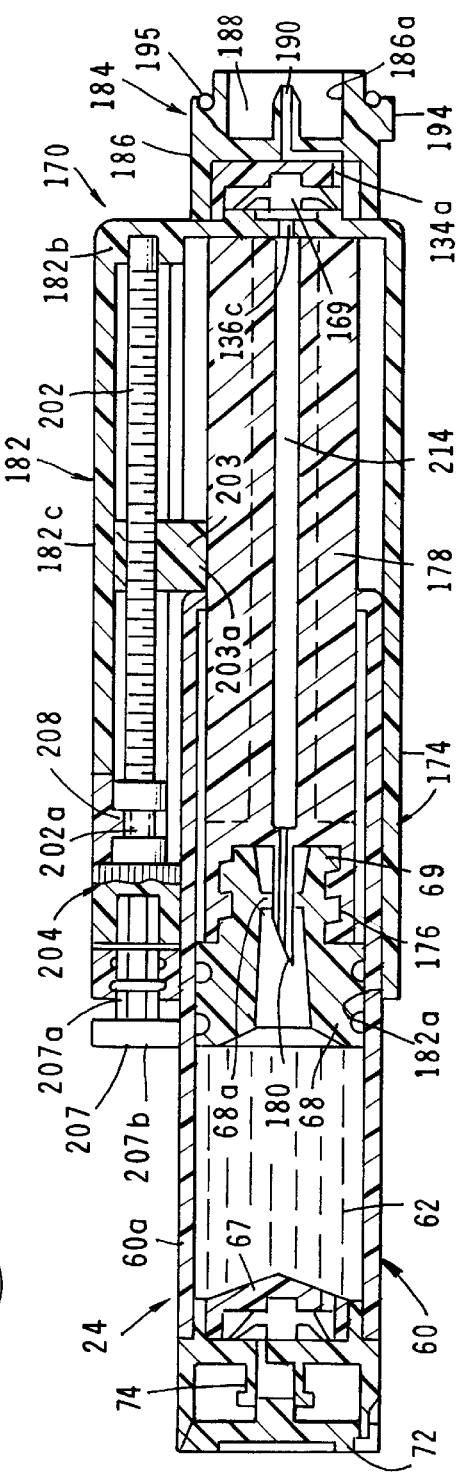

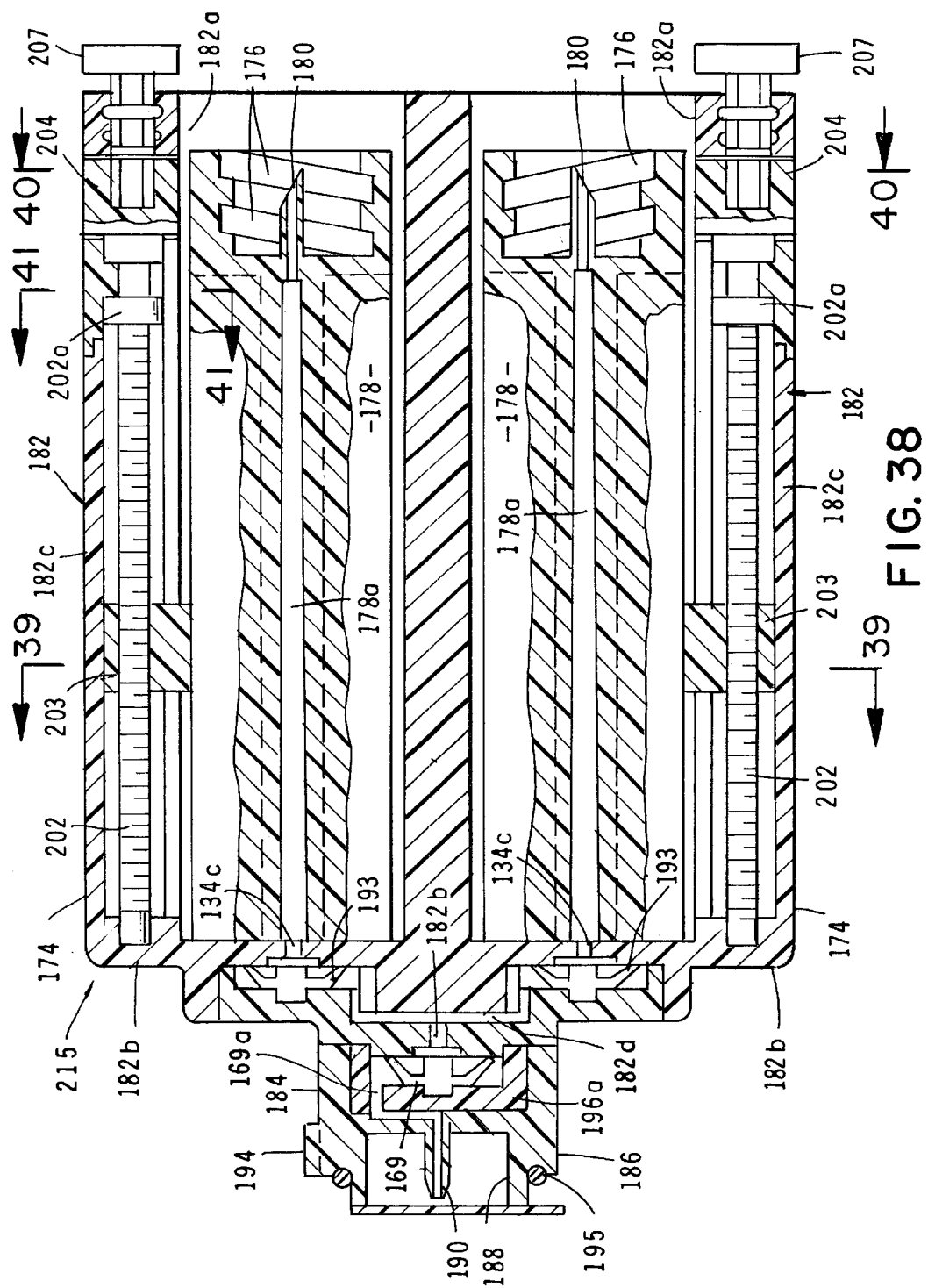

FLUID DELIVERY APPARATUS WITH RESERVOIR FILL ASSEMBLY

BACKGROUND OF THE INVENTION

This is a Continuation-In-Part Application of application, Ser. No. 09/250,036 filed Feb. 12, 1999, now U.S. Pat. No. 6,086,561 which is a Continuation-In-Part of Ser. No. 09/017,047 filed Feb. 2, 1998 which has now issued into U.S. Pat. No. 5,962,794, which is a Continuation-In-Part of Ser. No. 08/718,686 filed Sep. 24, 1996, now U.S. Pat. No. 5,721,382, which is a Continuation-In-Part of application, Ser. No. 08/432,220, filed May 1, 1995, now abandoned.

FIELD OF THE INVENTION

The present invention relates generally to fluid delivery devices. More particularly, the invention concerns an improved apparatus, including a fluid dispenser having visual flow indicator means, for infusing medicinal agents into an ambulatory patient at specific rates over extended periods of time and a novel reservoir fill assembly for controllably filling the reservoir of the fluid dispenser, including a fill assembly for filling the reservoir in the field.

DISCUSSION OF THE INVENTION

Many medicinal agents require an intravenous route for administration thus bypassing the digestive system and precluding degradation by the catalytic enzymes in the digestive tract and the liver. The use of more potent medications at elevated concentrations has also increased the need for accuracy in controlling the delivery of such drugs. The delivery device, while not an active pharmacologic agent, may enhance the activity of the drug by mediating its therapeutic effectiveness. Certain classes of new pharmacologic agents possess a very narrow range of therapeutic effectiveness, for instance, too small a dose results in no effect, while too great a dose results in toxic reaction.

In the past, prolonged infusion of fluids has generally been accomplished using gravity flow methods, which typically involve the use of intravenous administration sets and the familiar bottle suspended above the patient. Such methods are cumbersome, imprecise and require bed confinement of the patient. Periodic monitoring of the apparatus by the nurse or doctor is required to detect malfunctions of the infusion apparatus.

Devices from which liquid is expelled from a relatively thick-walled bladder by internal stresses within the distended bladder are well known in the prior art. Such bladder, or "balloon" type, devices are described in U.S. Pat. No. 3,469,578, issued to Bierman and in U.S. Pat. No. 4,318,400, issued to Perry. The devices of the aforementioned patents also disclose the use of fluid flow restrictors external of the bladder for regulating the rate of fluid flow from the bladder.

The prior art bladder type infusion devices are not without drawbacks. Generally, because of the very nature of bladder or "balloon" configuration, the devices are unwieldy and are difficult and expensive to manufacture and use. Further, the devices are somewhat unreliable and their fluid discharge rates are frequently imprecise.

The apparatus of the present invention overcomes many of the drawbacks of the prior art by eliminating the bladder and making use of recently developed elastomeric films and similar materials, which, in cooperation with a base define a fluid chamber that contains the fluid which is to be dispensed. The elastomeric film membrane controllably forces fluid within the chamber into fluid flow channels provided in the base.

The elastomeric film materials used in the apparatus of the present invention, as well as various alternate constructions of the apparatus, are described in detail in U.S. Pat. No. 5,205,820 issued to one of the present inventors. Therefore, U.S. Pat. No. 5,205,820 is hereby incorporated by reference in its entirety as though fully set forth herein. U.S. Pat. No. 5,721,382, also issued to one of the present inventors, describes various alternate constructions and modified physical embodiments of the invention, including the provision of a novel fluid actuated indicator means for visually indicating fluid flow from the device. This latter U.S. Pat. No. 5,721,382 is also hereby incorporated by reference in its entirety as though fully set forth herein.

Another somewhat similar apparatus to that of the present invention is described in application Ser. No. 09/250,036 filed by the present inventors on Feb. 12, 1999. Because of the pertinence of this application, U.S. Ser. No. 09/250,036, now U.S. Pat. No. 6,086,561, is hereby incorporated by reference as through fully set forth herein.

The apparatus of the present invention can be used with minimal professional assistance in an alternate health care environment, such as the home. By way of example, devices of the invention can be comfortably and conveniently removably affixed to the patient's clothing or to the patient's body and can be used for the continuous infusion of antibiotics, hormones, steroids, blood clotting agents, analgesics including morphine, and like medicinal agents. Similarly, the devices can be used for I-V chemotherapy and can accurately deliver fluids to the patient in precisely the correct quantities and at extended microfusion rates over time.

One form of the apparatus of the present invention uniquely permits the reservoir of the fluid-dispensing component to be filled in the field.

Another form of the apparatus of the invention includes novel volume control means for precisely controlling the volume of fluid to be introduced into the reservoir of the dispensing component.

SUMMARY OF THE INVENTION

It is an object of the present invention to provide an apparatus for delivering fluids at a precisely controlled rate which comprises a fluid dispensing component having a fluid reservoir for containing the fluids to be delivered and a reservoir fill component which can be removably interconnected with the fluid dispensing component. More particularly, it is an object of the invention to provide such an apparatus in which the reservoir fill component can be used in the field to controllably fill the reservoir of the dispensing component and in which the dispensing component can be used for the precise infusion of pharmaceutical fluids to an ambulatory patient at controlled rates.

It is another object of the invention to provide an apparatus of the aforementioned character which is highly reliable and easy-to-use by lay persons in a non-hospital environment.

A further object of the invention is to provide an accurate and highly reliable fluid delivery device which can be manufactured inexpensively in large volume by automated machinery.

Another object of the invention is to provide an apparatus of the type described in the preceding paragraphs which includes novel volume control means for precisely controlling the volume of medicinal fluids that are introduced into the reservoir of the fluid dispensing component.

Another object of the invention is to provide an apparatus of the character described that includes first and second reservoir fill assemblies for filling the fluid reservoir of the fluid dispensing component.

Another object of the invention is to provide an apparatus of the aforementioned character which includes a delivery component and a filling component which can be operably interconnected with the delivery component to enable expeditious filling in the field of the reservoir of the delivery component. More particularly, the first fill assembly permits the pharmacist to aseptically fill the container under patient-specific-variable volume and concentration of medicament. In this way, body mass index requirements can be met for selected agents as, for example, immuno- and chemo-therapeutic agents.

Another object of the invention is to provide a device of the class described in the preceding paragraphs in which the dispenser component embodies a highly novel fluid flow indicator that provides a readily discernible visual indication of fluid flow status through the device.

Another object of the invention is to provide a device of the aforementioned character in which the dispenser component includes a novel infusion means in the form of delivery line assembly, which can be interconnected with the dispenser.

Another object of the present invention is to provide a second reservoir fill means in which the container of the fill means is partially received within a novel adapter subassembly that can be sealably connected to an outlet port provided in the base of the fluid dispensing device.

Another object of the invention is to provide first and second reservoir fill assemblies for use with the fluid dispenser subassembly of the apparatus which are easy to use, are inexpensive to manufacture, and which maintain the container of the fill assemblies in a substantially aseptic condition until time of use.

Other objects of the invention are set forth in U.S. Pat. Nos. 5,205,820 and 5,721,382 and 6,086,561 all of which are incorporated herein by reference. Still further objects will become more apparent from the discussion that follows.

By way of summary, the fluid delivery apparatus of the present form of the invention comprises four cooperating components, namely a fluid delivery apparatus or dispenser, an infusion means for infusing medicaments into the patient and first and second reservoir fill assemblies which can be coupled with the fluid dispenser component for filling the fluid reservoir thereof. The fluid dispenser, which readily lends itself to automated manufacture, is generally similar to that described in U.S. Pat. No. 5,721,382 and includes a base and a stored energy means comprising at least one distendable elastomeric membrane which cooperates with the base to form a fluid reservoir. The fluid dispenser includes a highly novel fluid flow indicator means which is substantially similar to that described in U.S. Pat. No. 6,086,561 and comprises a mechanical fluid flow indicator that provides a clear visual indication of normal fluid flow and absence of fluid flow from the fluid reservoir. One form of the reservoir fill means of the invention also uniquely includes volume control means for controlling the volume of fluid to be introduced into the reservoir of the fluid dispenser by one of the fill means of the invention.

BRIEF DESCRIPTION OF THE DRAWINGS

FIG. 2 is a cross-sectional view taken along lines 2—2 of FIG. 1.

FIG. 3 is a fragmentary, top plan view of a portion of the delivery component and of the first fill means of the invention.

FIG. 4 is a right-end view of the device shown in FIG. 3.

FIG. 5 is a fragmentary, side-elevational, cross-sectional view of the base of the fluid delivery component of the invention.

FIG. 5A is a fragmentary, cross-sectional view of the pusher means of the base component shown in FIG. 5, partly broken away to show internal construction.

FIG. 5B is a right-end view of the pusher member shown in FIG. 5A.

FIG. 7 is a cross-sectional view similar to FIG. 6, but showing the fluid chamber of the first fill means having been filled using a syringe-type device.

FIG. 8 is a fragmentary, cross-sectional view of the right-end portion of the first fill means shown in FIG. 6 illustrating the manner of opening and closing the end panel of the device to enable filling of the fill means in the field.

FIG. 9 is a fragmentary, cross-sectional view of an alternate form of first fill means of the invention.

FIG. 9A is a fragmentary, cross-sectional, exploded view of the first fill means shown in FIG. 9 illustrating the removal of the end cap thereof to gain access to the fill port of the fill means.

FIG. 9B is an exploded, cross-sectional view of a portion of the first fill means shown in FIG. 9.

FIG. 10 is a fragmentary, cross-sectional view of still another form of first fill means of the invention.

FIG. 11 is a fragmentary, cross-sectional view similar to FIG. 10, but showing the removal of the end cap of the device to gain access to a slit septum used to fill the fluid chamber of the device.

FIG. 12 is a generally perspective view of the form of the first fill means shown in FIG. 6.

FIG. 13 is a generally perspective view of the alternate form of first fill means of the invention shown in FIG. 9A.

FIG. 14 is a generally perspective, exploded view of the first fill means shown in FIG. 10.

FIG. 15 is a generally perspective, exploded view of the fill means shown in FIG. 13.

FIG. 16 is a generally perspective view of one form of the second or adapter fill means of the invention.

FIG. 16A is a cross-sectional view of the adapter fill means shown in FIG. 16.

FIG. 18 is a top plan view of the adapter fill assembly shown in FIGS. 16 and 17.

FIG. 19 is a side elevational, cross-sectional view of the adapter fill assembly shown in FIG. 18.

FIG. 20 is a cross-sectional view taken along lines 20—20 of FIG. 19.

FIG. 21 is an enlarged cross-sectional view of the area designated in FIG. 20 by the numeral 21.

FIG. 22 is a top plan view of one form of the stop member of the apparatus for controlling the extent of entry of the container assembly into the adapter assembly.

FIG. 23 is a side-elevational view of the stop member shown in FIG. 22.

FIG. 24 is a generally perspective view of still another form of adapter fill assembly of the invention.

FIG. 24A is a cross-sectional view taken along lines 24A—24A of FIG. 24.

FIG. 38 is a view taken along lines 38—38 of FIG. 37.

DESCRIPTION OF THE INVENTION

Figure 1:
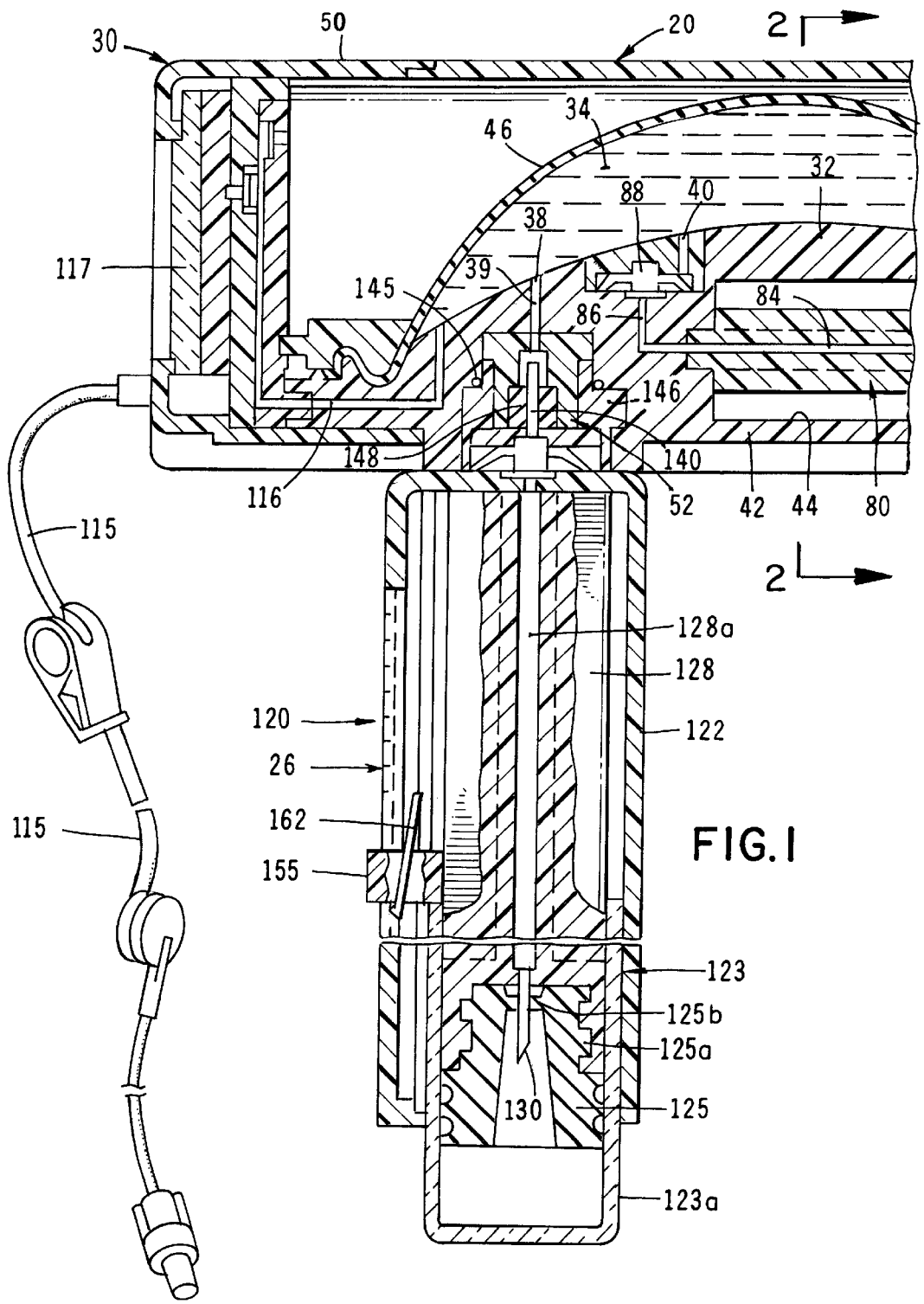
FIG. 1 is a side-elevational, cross-sectional view of one form of the apparatus of the invention, which includes a fluid delivery component and first and second fill means for filling the reservoir of the fluid delivery component.

Referring to the drawings and particularly to FIGS. 1 through 5, one form of the apparatus of the invention for controlled delivery of medicinal fluid to a patient is there shown and generally designated by the numeral 20. The apparatus here comprises four major components, namely a fluid delivery component 22, first and second fill assemblies 24 and 26 respectively and infusion means for infusing medicinal fluids into the patient. The construction of the first and second fill assemblies 24 and 26 will be described hereinafter.

The fluid delivery component 22 includes a housing 30 having a base assembly 32 and a stored energy means which cooperates with the base assembly to form a fluid reservoir 34 (FIG. 1). Reservoir 34 is provided with first and second inlets 38 and 40 respectively. Base assembly 32 also includes a base 42 having a receiving chamber 44 formed therein (FIG. 5). The stored energy means of this form of the invention comprises an elastomeric membrane 46 which is clamped to base 42 by means of a clamping ring 48 in a manner similar to that described in incorporated by reference U.S. Pat. No. 5,840,071. Clamping ring 48, along with elastomeric membrane 46 is enclosed by a cover 50 of the configuration shown in FIGS. 1 and 2. As best seen in FIG. 1, receiving chamber 44 of base 42 is adapted to controllably receive the first fill means or assembly 24 of the invention to permit controlled filling of the reservoir of the device via inlet 40. Base 42 also includes a fill port assembly 52 to which the second fill means or assembly 26 of the invention can be removably interconnected. As indicated in FIG. 1, fill port assembly 52 communicates with inlet 38 via a fluid passageway 39. The construction and operation of the important fill port assembly 52 will presently be described.

Turning particularly to FIGS. 6, 6A, 7, 8 and 12, one form of the first fill assembly 24 of the invention can be seen to comprise a container subassembly 60 that includes a container, or vial portion 60a having a fluid chamber 62 for containing an injectable fluid "F". As shown in FIG. 12, container subassembly 60 can be provided with a medicament identification label 63. Fluid chamber 62 is provided with first and second open ends 62a and 62b. First end 62a is closed by an apertured, self-venting peel away aseptic cover 64. Second open end 62b is sealably closed by closure means here provided in the form of a closure subassembly 66. Displacement means, here shown as a plunger 68 is telescopically movable within chamber 62 of container subassembly 60 in the manner indicated in FIGS. 6 and 7.

Figure 6:
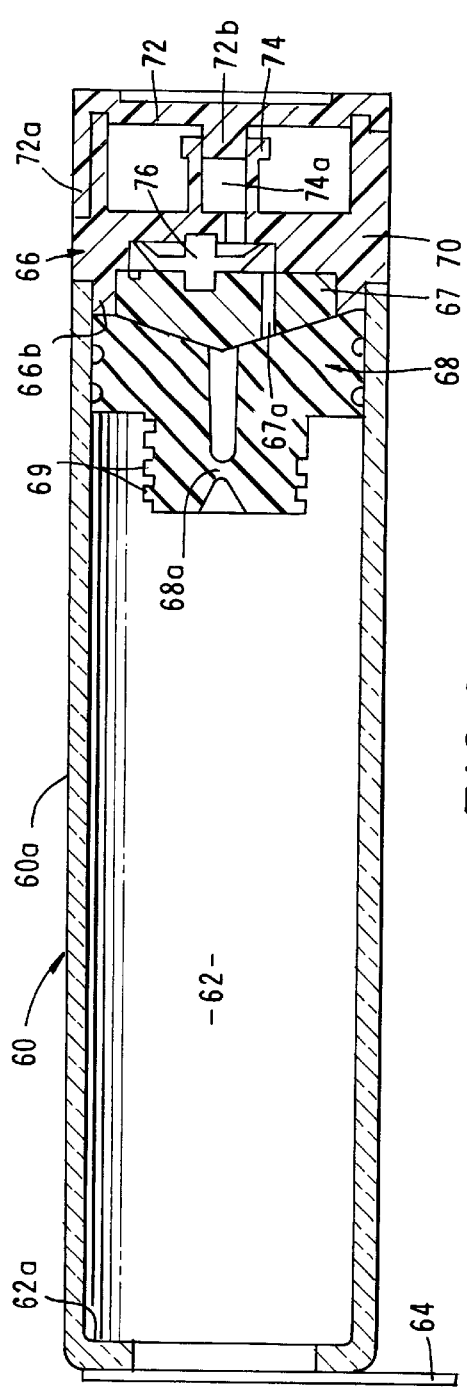
FIG. 6 is an enlarged, side-elevational, cross-sectional view of one form of the first fill means of the invention.
Figure 6A:
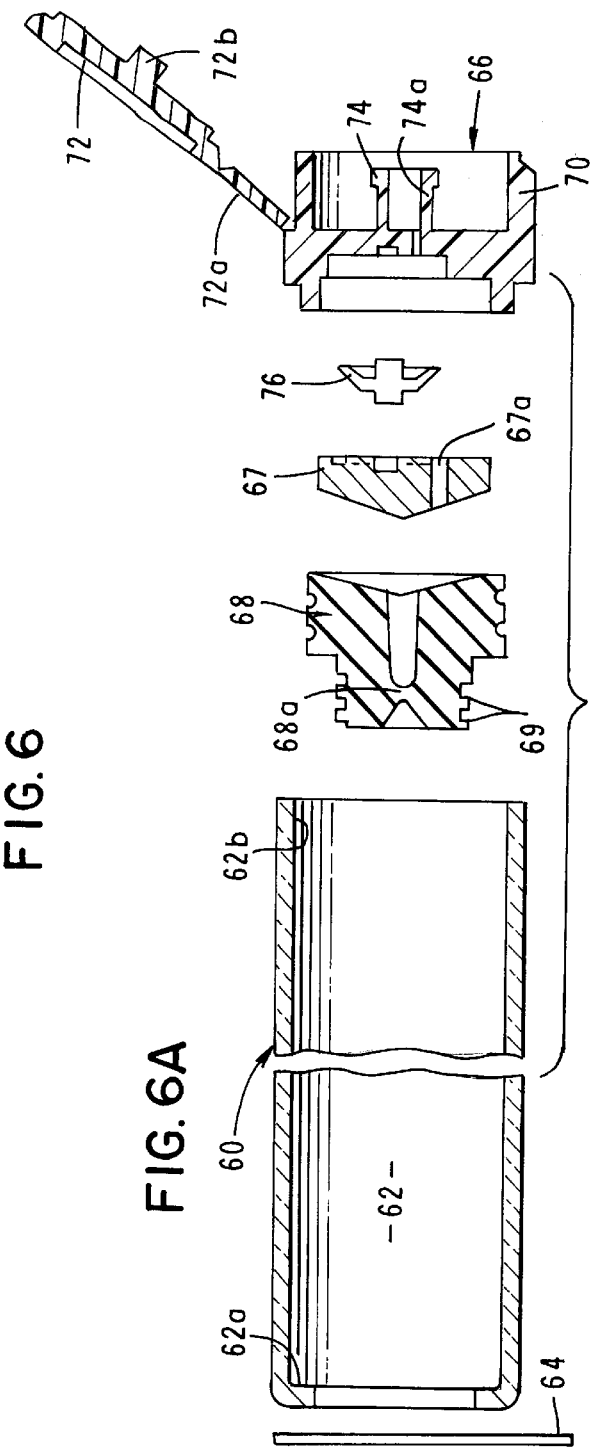
FIG. 6A is an exploded, cross sectional view of the first fill means shown in FIG. 6.

In the manner shown in FIGS. 6, 7, and 8 closure subassembly 66 is sealably connected to container 60a and to a conically shaped connector member 67, which has a fluid passageway 67a. Closure assembly 66 comprises a generally cylindrically shaped closure housing 70 and a closure panel 72 that is hingedly connected to housing 70 by a living hinge 72a. Panel 72 is movable from the closed position shown in FIG. 6 to the open position in FIG. 7. Also comprising a part of closure subassembly 66 is connector means for interconnecting fluid chamber 62 of container 60a with a source of medicinal fluid. In the form of the invention shown in FIGS. 6 and 7 this connector means comprises a rearwardly extending male luer connector 74. As shown in FIG. 6, when panel 72 is in the closed position, a sealing protuberance 72b formed on end panel 72 will be sealably received within passageway 74a of connector 74 to sealably close the passageway. When panel 72 is raised in the manner shown in FIG. 7, connector 74 becomes accessible and can be interconnected with a source of fluid such as a syringe S that includes a female connector S-1. As chamber 62 is filled with fluid, plunger 68 will be moved from the first position shown in FIG. 6 to the second position shown in FIG. 7. Also forming a part of closure subassembly 66 is valve means for controlling fluid flow toward to chamber 62 of container 60a. In the present form of the invention this valve means comprises a conventional umbrella check valve 76.

Following filling of chamber 62 and removal of peel-away aseptic cover 64, container subassembly 60 can be telescopically inserted into receiving chamber 44 of base 42 and moved from a first extended position shown in FIG. 1 into a second fluid filling position. Disposed within chamber 44 is a pusher member 80 having the configuration shown in FIGS. 5A and 5B. Pusher member 80 functions to move plunger 68 within the fluid chamber 62 of the container subassembly as the container subassembly is inserted into chamber 44. During the mating of the first fill means with the fluid delivery component, the outer wall of vial 60*a* is closely received within chamber 44 as the container subassembly is moved inwardly or forwardly of the device housing. It is to be observed that when the container subassembly is originally mated with the delivery component in the manner shown in FIG. 1, threads 69 provided on plunger 68 will mate with internal threads 80*a* provided on pusher member 80 (FIG. 5A) and a pierceable wall 68*a* of plunger 68 of container subassembly 60 will move into piercing engagement with a hollow cannula 84 that is disposed centrally of pusher member 80.

Once the fluid flow path between the hollow cannula 84 and the fluid reservoir 34 of the delivery component 20 is thus created, via a passageway 86 formed in base 42, via a second check valve 88 mounted within base 42 and a via inlet 40, the reservoir can be filled as a result of an inward movement of the container subassembly 60 into receiving chamber 44. As the container subassembly moves inwardly, pusher member 80 will move plunger 68 rearwardly of chamber 62 causing the fluid contained therewithin to be forced outwardly thereof through hollow cannula 84 and into passageway 86. As the fluid enters inlet 40, elastomeric member 46 will be distended in the manner shown in FIG. 1 causing the buildup of internal stresses within the member tending to return it to a less distended position.

Referring next to FIGS. 9, 9A, 9B, 13 and 15, an alternative form of first fill means of the invention is there illustrated. This form of the invention is similar in many respects to that shown in FIGS. 1 through 8 and previously described herein and like numerals are used in FIGS. 9 and 9A to identify the like components shown in FIGS. 6, 7 and 8. As illustrated in FIGS. 9 and 9A this alternate form of first fill means of the invention also includes a container 60*a* having a fluid chamber 62. However, connected to container 60*a* is an alternative form of closure subassembly that is generally designated in FIGS. 9 and 9A by the numeral 89. Closure subassembly 89 is sealably connected to container 60*a* in the manner shown in FIGS. 9 and 9A and includes an externally threaded closure housing 89*a*. Closure housing 89*a* comprises a luer connector member 91 which is of the same general configuration as luer connector member 74. Closure subassembly 89 further includes an end closure cap 89*b* which is internally threaded so that it can be threadably interconnected with housing 89*a*. During the filling step, access to connector 91 is accomplished by threadably removing end cap 89*b* in the manner shown in FIGS. 9A and 15 so as to enable the interconnection therewith of a filling syringe, such as syringe S (FIG. 7).

Turning to FIG. 10, still another form of first fill means of the invention is there illustrated. This embodiment is similar in many respects to those previously described, and like numerals are used to identify like components. As before, this latest embodiment includes a container 60*a* having a fluid chamber 62. Connected to container 60*a* in the manner shown in FIG. 10 is a closure subassembly 90. Subassembly 90 supports check valve 76 in a manner shown in FIG. 10. As indicated in FIG. 10, in this latest form of the first fill means, subassembly 90 includes a housing 92 and a slit septum 94 which is sealably mounted within a collar 96 which is, in turn, connected to housing 92. Slit septum 94 is accessible by lifting hingedly mounted end panel 72 in the manner shown by the phantom lines of FIG. 10 so that the septum can be pierced by the cannula of a fill syringe of a character well known to those skilled in the art to effect a controlled filling of chamber 62.

Referring next to FIG. 11, still another form of first fill means of the invention is their illustrated. This form of the invention is similar in many respects to that previously described and like numerals are used in FIG. 11 to identify the like components shown in FIGS. 10. As illustrated in FIG. 11, this alternate form of first fill means also includes a container 60*a* having a fluid chamber 62. Connected to container 60*a* is an alternative form of closure subassembly generally designated as 104. Closure subassembly 104 is connected to container 60*a* in the manner shown in FIG. 11 and includes a closure housing 106. Connected to closure housing 106 is an externally threaded septum housing 108 within which a slit septum 110 is sealably mounted. Closure housing 106 is connected to a connector member 67 which, in turn, is connected to container 60*a* in the manner shown in FIG. 11. Adapted to threadably mate with septum housing 108 is an end closure cap 112. End closure cap 112 is internally threaded so that it can be threadably interconnected with septum housing 108 in the manner indicated in FIG. 11. During the filling step, access to septum 110 is accomplished by threadably removing end cap 112 so as to enable piercing of slit septum 110 by a cannula of a syringe or like filling component.

Once the reservoir has been filled and the container subassembly has been appropriately mated with delivery component 20, the apparatus will remain in this readied condition until the administration line 115 of the infusion means of the device is opened. Once the administration line has been opened, the stored energy means or membrane 46 will tend to return to a less distended condition causing fluid to flow outwardly of the apparatus via passageway 116, which is formed in base 42, via the novel indicator means of the invention (FIG. 1). As previously mentioned, the indicator means, which is generally identified in FIG. 1 by the numeral 117, is of identical construction to that shown and described in incorporated by reference application Ser. No. 09/250,036. Reference to this application should be made for a description of the construction and operation of the indicator means.

Considering next the second, or adapter fill assembly 26 of the invention, this assembly is also used to fill reservoir 34 and comprises a novel fluid transport assembly 120 of the general configuration shown in FIGS. 1 and 16. Referring to FIGS. 16, 17, 18 and 19, it is to be noted that fluid transport assembly 120 is specially designed to be mated with fill port assembly 52 formed in base 42 of the fluid dispenser component 20. As best seen in FIGS. 16 and 16A, fluid transport assembly 120 comprises a fill assembly 26 which is substantially identical to that shown in FIG. 1 and includes an adapter assembly 122 that telescopically accepts a closed end container assembly 123.

Turning to FIGS. 16, 16A and 19, it is to be noted that threads 125*a* provided on a plunger 125 of container subassembly 123 of the second fill assembly can be threadably connected to threads 126 provided on a pusher member 128 of adapter assembly 122. Pusher member 128 also includes a cannula 130 which is constructed and arranged to pierce the central wall 125*b* of plunger 125 when the container subassembly 123 is mated with the adapter assembly 122. Cannula 130 communicates with fluid chamber of the container 123*a* of container subassembly 123 and here comprises a part of the adapter flow control means of the adapter assembly for controlling fluid flow toward reservoir 34.

As best seen in FIGS. 16, 16A and 19, adapter subassembly 122 comprises a hollow container receiving housing 132 having a first open end 132*a* and a second closed end 132*b*. Container subassembly 123 of fill assembly 26 is telescopically receivable within open end 132*a* of housing 132 so that container 123*a* thereof can be moved from a first extended position shown in FIG. 16 to a second advanced position wherein container 123*a* is at least partially encapsulated within housing 132.

Also forming a part of the adapter assembly of the invention is a connector means or cap assembly 134 (FIG. 19) which is connected to body portion 132 in the manner shown in FIG. 19. Cap assembly 134 includes a generally cylindrical exterior wall 136, the interior surface 136*a* of which forms a chamber 138 into which a cannula 140 extends. To interconnect second fill assembly 120 with the fluid delivery apparatus, the barrel-like portion of closure cap 134 of the second fill assembly is mated with fill port 52 formed in base 42. As the barrel-like portion enters the lower portion of the fill port, the circumferentially spaced tabs 144 of closure cap 134 (see FIGS. 16 and 19) are received within circumferentially spaced tab receiving slots 146 formed in the fill port (FIG. 1). Cap 134 is provided with an elastomeric O-ring 145 so that an inward pressure exerted on the adapter assembly will effect a secure interconnection and sterile coupling of the second fill assembly with the fill port 52. As the second fill assembly 120 is mated with the delivery component, cannula 140 of the fill assembly will pierce a pierceable septum 148 which is mounted within fill port 52 in the manner shown in FIG. 1.

Figure 17:
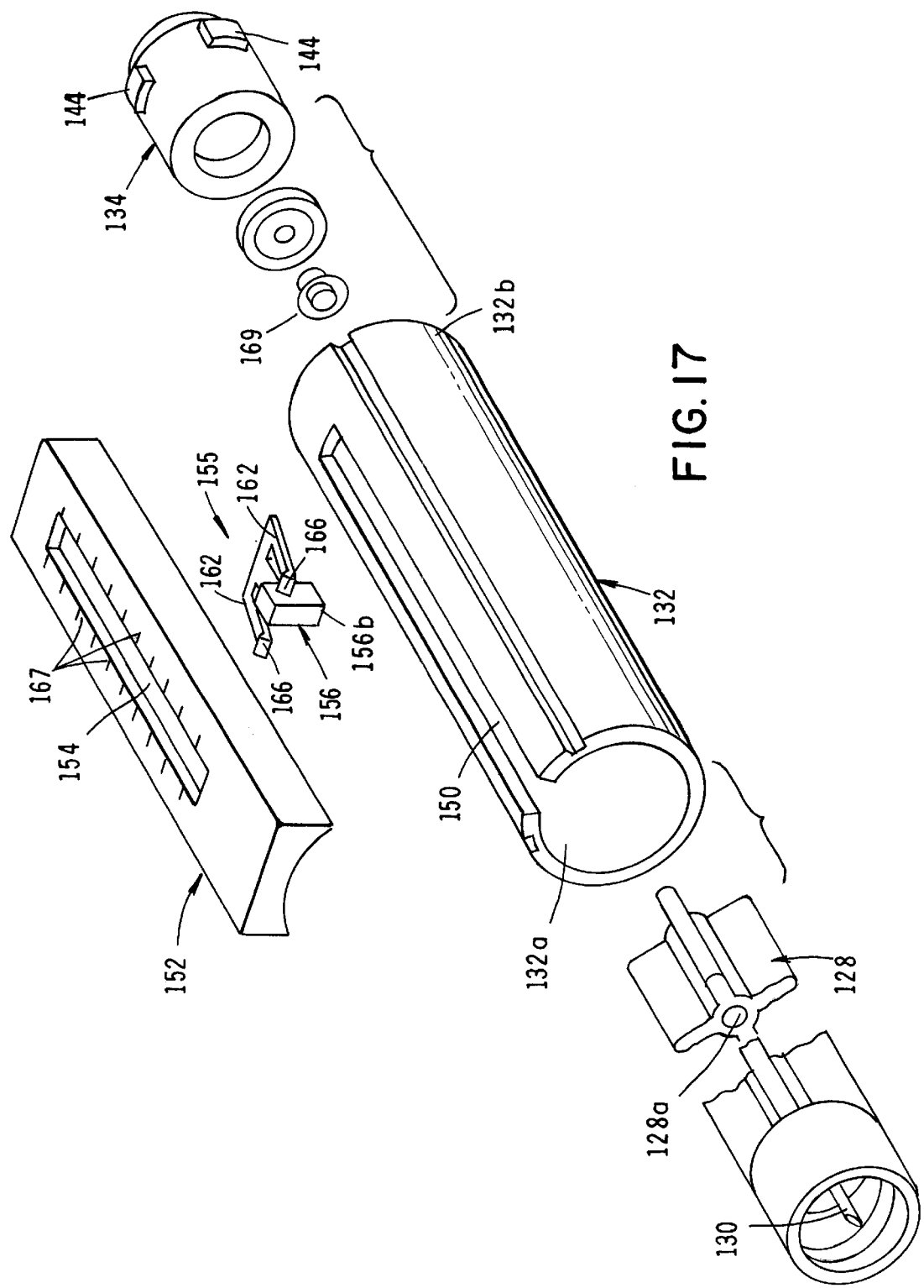
FIG. 17 is a generally perspective, exploded view of one form of the adapter fill assembly shown in FIG. 16.

As best seen by referring to FIG. 17, container receiving housing 132 is provided with an elongated track 150. Connected to container receiving housing 132 is an indicator housing 152 having an elongated track 154 that is aligned with and overlays track 150 in the manner shown in FIG. 20. Forming an important aspect of this latest embodiment of the invention is volume control means for controlling the volume of fluid to be introduced into fluid reservoir 34 of the delivery component 20 by means of fill assembly 120. This volume control means comprises a stop means here provided as a stop member assembly 155 which includes a push button 156 that is slidably movable within elongated tracks 150 and 154 from a first position to a second position. In a manner presently to be described, push button 156 is constructed and arranged to be engaged by container 123*a* of the fill assembly as the container is introduced into container receiving housing 132 and, in this way, functions to limit the extent of travel of the container within the container receiving housing 132. By this mechanism, the volume of fluid contained within container 123*a* that is to be introduced into reservoir 34 of the fluid delivery component 20 can be precisely controlled.

Referring particularly to FIGS. 17 through 23, it is to be noted that push button 156 has an upper portion 156*a*, a lower portion 156*b*, and an intermediate portion 156*c*. Connected to intermediate portion 156*c* is locking means for locking the stop means in position. This locking means here comprises a longitudinally extending connector member 160 (FIG. 22) to which a pair of longitudinally extending arms 162 are connected. Arms 162 which comprise the biasing means of this form of the invention, are resiliently movable relative to connector member 160 so that angularly shaped indexing tabs 166 that are provided proximate the ends of arms 162 are continuously urged into engagement with a plurality of longitudinally spaced apart locking teeth 168 that are formed on the interior surface of indicator housing 152 (FIG. 19).

With the construction described in the preceding paragraph, the stop member assembly 155 can be positioned longitudinally of container receiving housing 132 by imparting a downward force on push button 156 thus clearing tabs 166 from teeth 168 thereby enabling the assembly to be moved forwardly or rearwardly of tracks 150 and 154 with tabs 166 slidably moving within a channel 153 (see FIGS. 16A, 19 and 21). When the assembly is in the desired position, a release of the downward pressure exerted on push button 156 will cause indexing tabs 166 to, once again, lockably engage locking teeth 168 to lock assembly 155 in place. With the assembly thusly locked in place by the locking means, the extent of entry of container 123*a* will be positively controlled as will the volume of fluid that will be introduced into reservoir 34. Provided on either side of track 154 are indicating indicia 167 which indicate to the user the volume of fluid that will be introduced into reservoir 34 at a particular setting of the stop assembly 155 within tracks 150 and 154.

With the stop assembly properly positioned, container 123*a* can be moved into housing 132 until the container engages the lower portion 156*b* of push button 156. As the container moves telescopically inward of housing 132, fluid will flow from the container into cannula 130, into central passageway 128*a* formed in pusher member 128, into a stub passageway 132*c* and into cannula 140 via a conventional umbrella check valve 169 which is mounted within cap 134 (FIG. 19) and via passageway 134*a*. Fluid will then flow through cannula 140 into passageway 39 of base 42 and finally into reservoir 34. As the fluid under pressure enters reservoir 34, membrane 46 will be distended in the manner shown in FIG. 1.

Turning next to FIGS. 24 through 34, an alternate form of the second, or adapter fill means of the invention is there shown and generally designated by the numeral 170. This fill means, which is also used to fill reservoir 34, is of a general configuration shown in FIGS. 24, 25, and 26. Referring particularly to FIG. 24, it is to be noted that fill means 170 is also specially designed to be sealably mated with fill port assembly 52 of the fluid delivery component 20. As illustrated in FIG. 24, fill means 170 comprises a fill assembly 24 which is identical to that previously described and an adapter assembly 174 which telescopically accepts container subassembly 60 of fill assembly 24.

Figure 26:
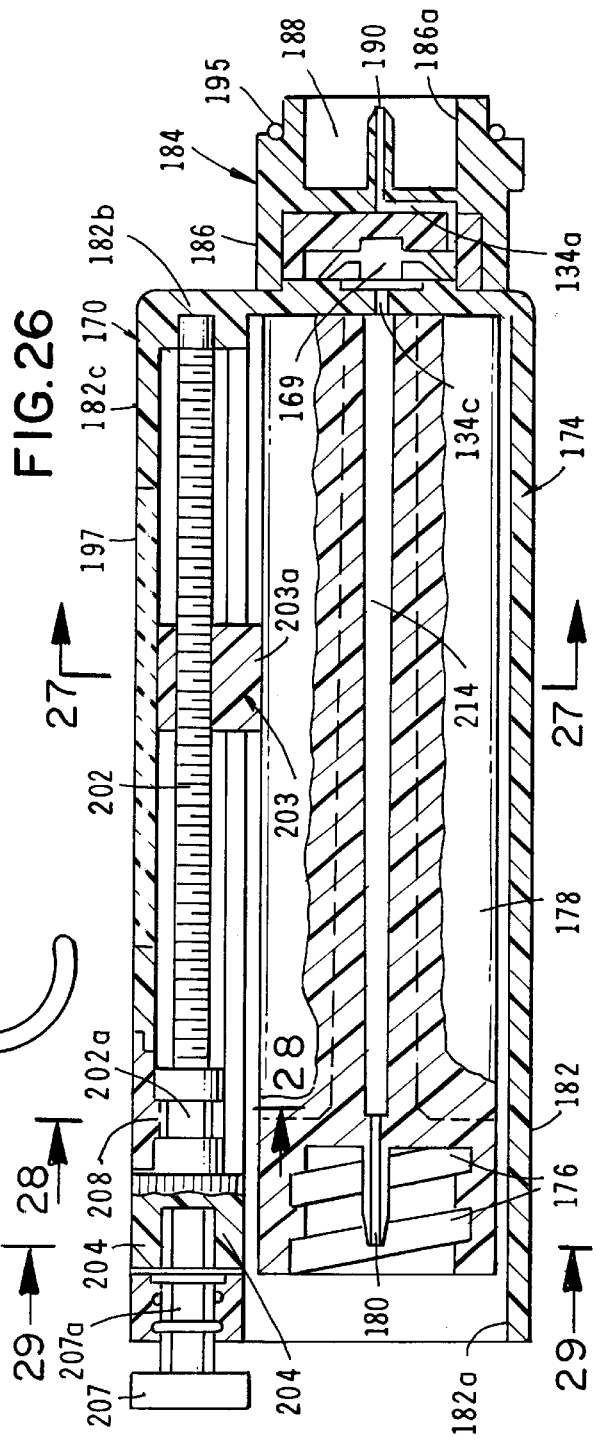
FIG. 26 is a view taken along lines 26—26 of FIG. 25.
Figure 27:
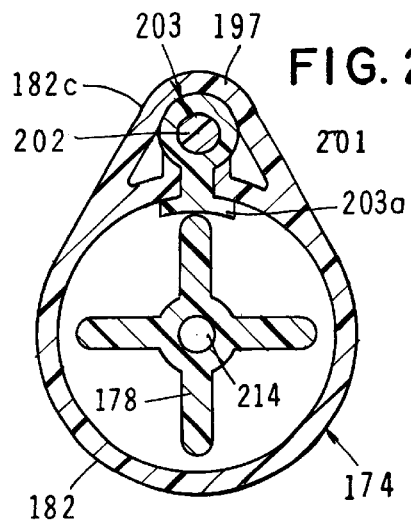
FIG. 27 is a cross-sectional view taken along lines 27—27 of FIG. 26.

As before, threads 69 provided on plunger 68 of the container subassembly 60 (FIG. 6) can be threadably connected to threads 176 provided on a pusher member 178 which comprises a part of adapter assembly 174 (FIG. 26). Pusher member 178 also includes a cannula 180, that is constructed and arranged to pierce the central wall 68*a* of plunger 68 when the container subassembly 60 is mated with the adapter assembly 174 (FIG. 6). Cannula 180 here comprises a part of the adapter flow control means of the adapter assembly for controlling fluid flow toward reservoir 34.

Referring particularly to FIGS. 25, 26, 27, and 28, it can be seen that adapter subassembly 174 comprises a generally cylindrically shaped hollow container receiving housing 182 having a first open end 182*a* and a second closed end 182*b*. Container subassembly 60 of the fill assembly is telescopically receivable within open end 182*a* of housing 182 so that the container component 60*a* thereof can be moved from a first extended position shown in FIG. 24 to a second advanced position wherein container 60 is at least partially encapsulated within housing 182.

Also forming a part of the adapter assembly of this latest form of the invention is a connector means or cap assembly 184 (FIG. 24) which is connected to body portion 182 in the manner shown in FIG. 26. Cap assembly 184 includes a generally cylindrical exterior wall 186, the interior surface 186a of which forms a chamber 188 into which a cannula 190 extends. To interconnect fill means 170 with the fluid delivery component 20, the barrel-like portion of closure cap 184 of the fill means is sealably mated with fill port 52 formed in base 42. As the barrel-like portion enters the lower portion of the fill port, the circumferentially spaced tabs 194 of closure cap 184 (see FIGS. 24 and 26) are received within circumferentially spaced tab receiving slots 146 formed in the fill port (FIG. 1). As before, cap 184 is provided with an elastomeric O-ring 195 so that an inward pressure exerted on the adapter assembly will effect a secure interconnection and sterile coupling of the fill means with the fill port 52. As the fill means 170 is mated with the delivery component, cannula 190 of the fill assembly will pierce the pierceable septum 148 which is mounted within fill port 52.

Figure 28:
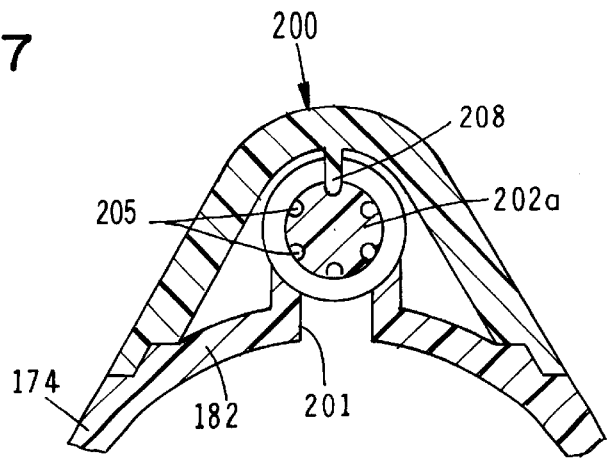
FIG. 28 is an enlarged cross-sectional view taken along lines 28—28 of FIG. 26.
Figure 29:
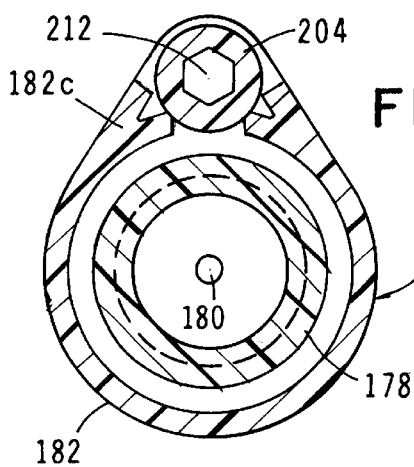
FIG. 29 is a cross-sectional view taken along lines 29—29 of FIG. 26.
Figure 31:
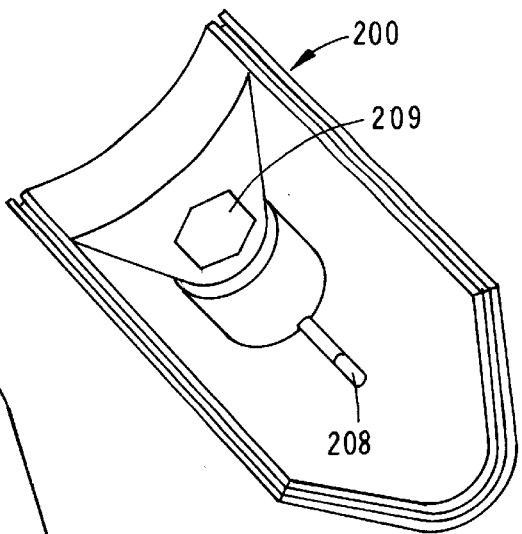
FIG. 31 is a generally perspective bottom view of the indicator housing shown in FIG. 30.

As best seen by referring to FIGS. 25 through 32, container receiving housing 182 includes an upper, curved portion 182c which is provided with an elongated viewing window 197, the purpose of which will presently be described. Connected to container receiving housing 182 and forming a continuation of upper portion 182c is an indicator housing 200 that houses a portion of the volume control means of this latest form of the invention for controlling the volume of fluid to be introduced into reservoir 34 (FIG. 24). This volume control means here comprises an internally threaded stop member 203 that is movable along a longitudinally extending track 201 that is formed within housing 182 (FIG. 28). As will be described in greater detail hereinafter, stop member 203 is controllably movable along track 201 by an elongated, externally threaded operating shaft 202 that is journaled for rotation with housing 182 and is rotated by operating means, which here comprises a finger-engaging control knob 204.

Figure 32:
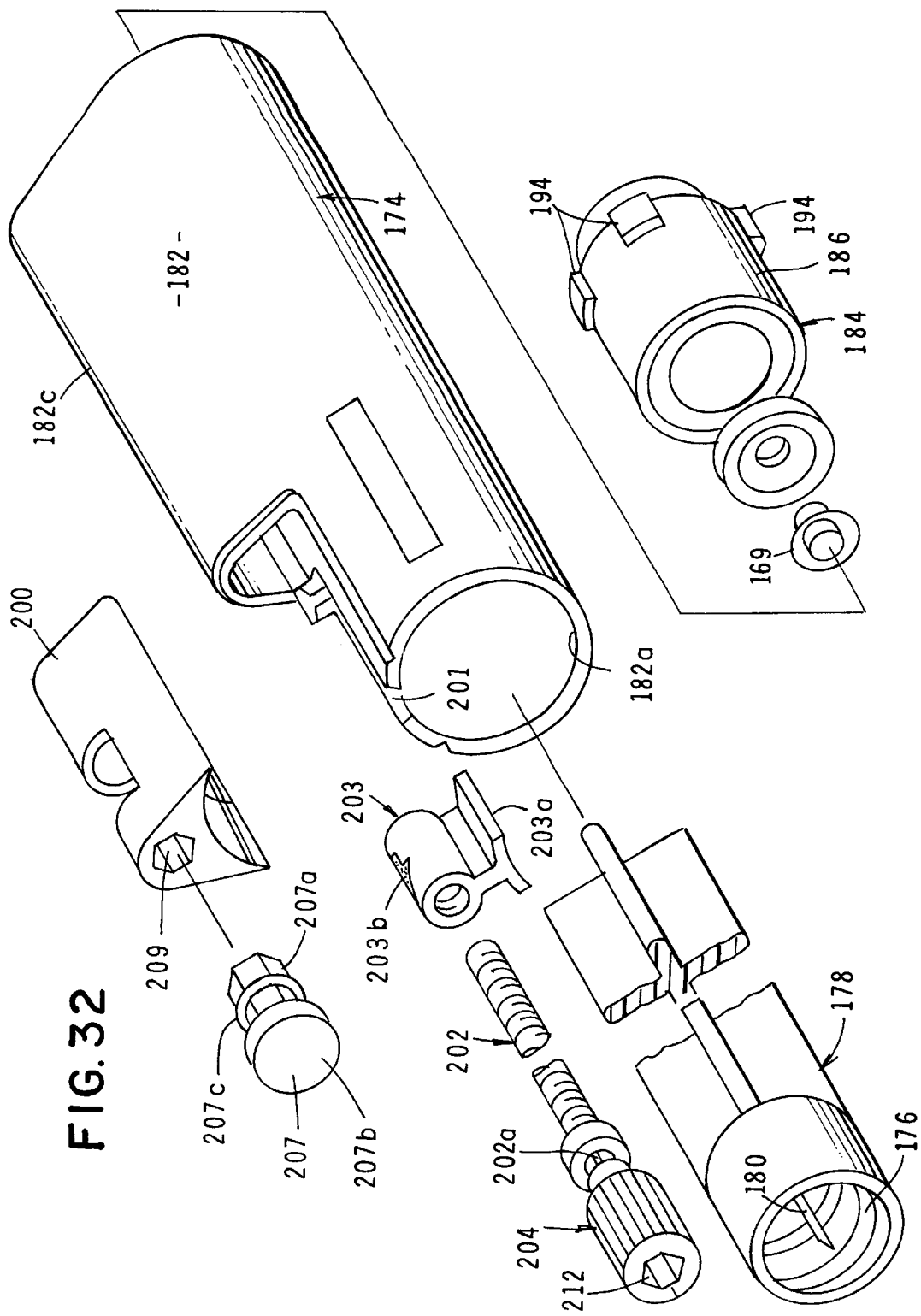
FIG. 32 is a generally perspective, exploded view of the adapter fill assembly shown in FIG. 24.

As best seen by referring to FIGS. 28 and 32, shaft 202 includes an enlarged diameter collar portion 202a that is provided with a plurality of circumferentially spaced indexing grooves 205. Received within grooves 205 is a spring tab 208 that extends downwardly from indicator housing 200 in the manner shown in FIGS. 28 and 31. Spring tab 208 functions to index operating shaft 202 within indicator housing 200.

Figure 25:
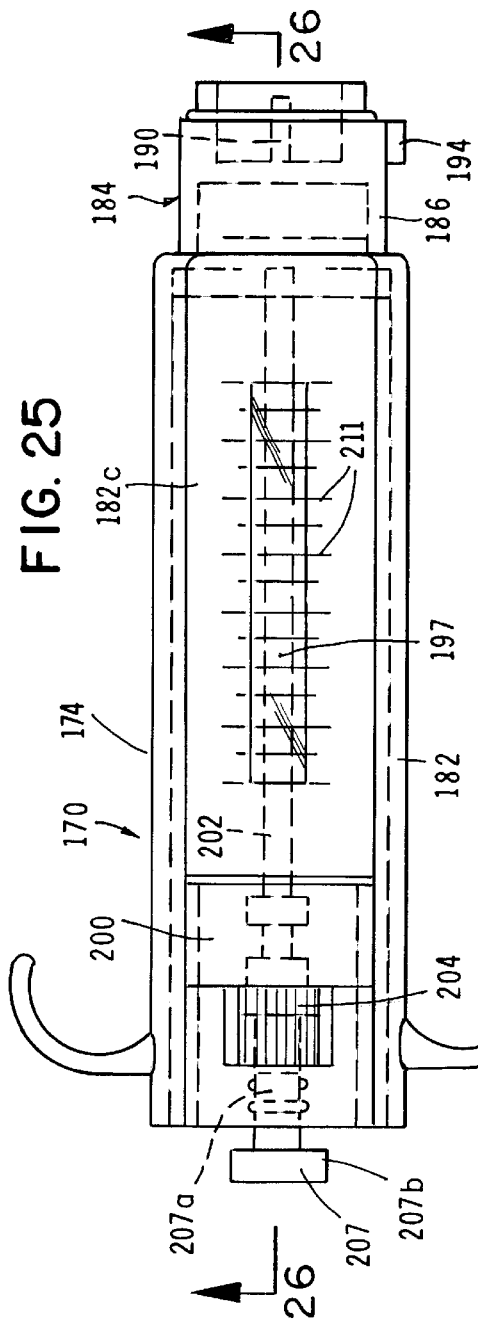
FIG. 25 is a top plan view of the fill assembly shown in FIG. 24.

With the construction described in the preceding paragraph and as illustrated in the drawings, rotation of control knob 204 will cause rotation of shaft 202 which, in turn, will cause forward or rearward movement of stop member 203 along track 201. As best seen by referring to FIGS. 26, 27 and 32 lower, portion 203a of stop member 203 extends downwardly into the interior of housing 182 so that it will be engaged by container subassembly 60 as the container subassembly is telescopically inserted into the open end 182a of hollow housing 182. Accordingly, the position of stop member 203 within hollow housing 182 will control the extent of travel of the container subassembly 60 within housing 182 and thusly will control the amount of fluid contained within container 60a of container subassembly 60 that will be introduced into reservoir 34 of the fluid delivery component 20. In this regard, stop member 203 is provided with an indicating arrow 203b (FIG. 32) which is visible through the viewing window 197 provided in housing portion 182c. As shown in FIG. 25, volume-indicating indicia 211 are provided along viewing window 197. The position of indicating arrow 203b relative to the volume-indicating indicia 211 indicates the volume of fluid that will be introduced into the reservoir of the fluid delivery component when the stop member 203 is moved to a selected position along track 201.

Figure 30:
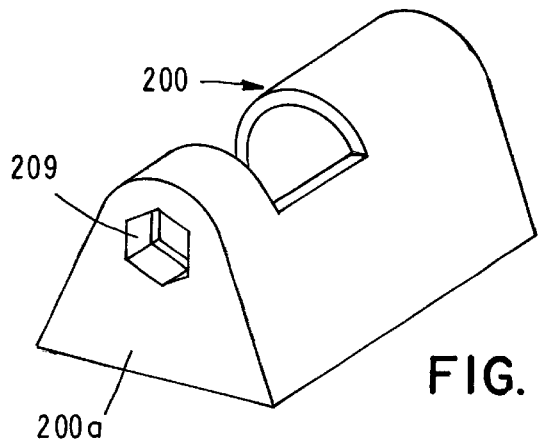
FIG. 30 is a generally perspective top view of the indicator housing of the fill assembly shown in FIG. 24.
Figure 33:
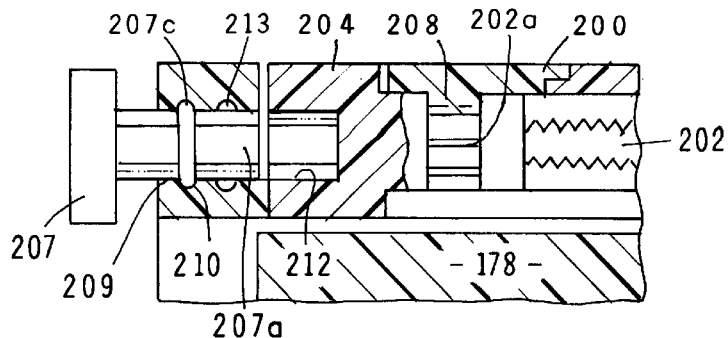
FIG. 33 is an enlarged, fragmentary, cross-sectional view of the control portion of the fill assembly for controlling the positioning of the stop member of the container assembly.
Figure 34:
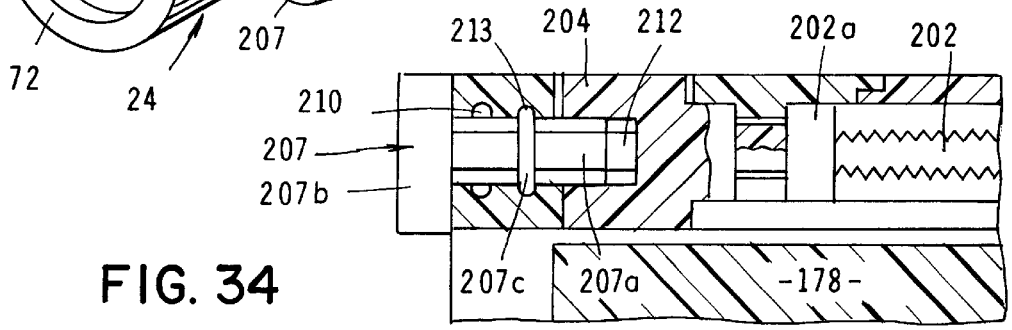
FIG. 34 is a cross-sectional view similar to FIG. 33, but showing the locking means of the assembly in a locked position locking the stop member of the fill adapter in a fixed position.

An important feature of this latest embodiment of the invention comprises locking means for locking stop member 203 in a selected position within a hollow housing 182. This locking means here comprises a locking pin 207 that is slidably carried within an opening 209 formed within indicator housing 200 (FIGS. 30, 33 and 34). Locking pin 207 includes a hexagonal-shaped shaft 207a that extends inwardly from a generally cylindrically shaped head portion 207b. Shaft 207a, which includes an enlarged diameter rib-like portion 207c is received within opening 209 in the manner shown in FIG. 33. When the locking means is in the first unlocked position shown in FIG. 33, rib-like portion 207c is received within a circumferentially extending groove 210 formed in opening 209. However, when the locking means is moved into the second locking position shown in FIG. 34, the inboard end of shaft 207a extends inwardly of a generally hexagon-shaped opening 212 formed in control knob 204 and rib-like portion 207c seats within a second circumferentially extending groove 213 formed within opening 209. As shown in FIG. 34, when the locking means is in the second locked position and the inboard end of shaft portion 207a is received within the opening 212, shaft 202 is securely locked against rotation. Accordingly, as long as the locking means is in the locked position shown in FIG. 34, the position of the locking member 203 within the housing 182 cannot be changed and the volume of fluid to be introduced into the reservoir of the fluid delivery component will remain unchanged.

In using the apparatus of this latest form of the invention, when the adapter fill means 170 is sealably interconnected with inlet port 52 of the fluid delivery component 20 and the stop member of the volume control means is appropriately set, an inward pressure exerted on container subassembly 60 will cause fluid to flow from fluid chamber 62 of the container into cannula 180, through a fluid passageway 214, formed in pusher member 178 and into cannula 190 via umbrella check valve 169 which is carried within cap assembly 184 (FIG. 26). Fluid will then flow into reservoir 34 via inlet 38 (FIG. 1).

Figure 35:
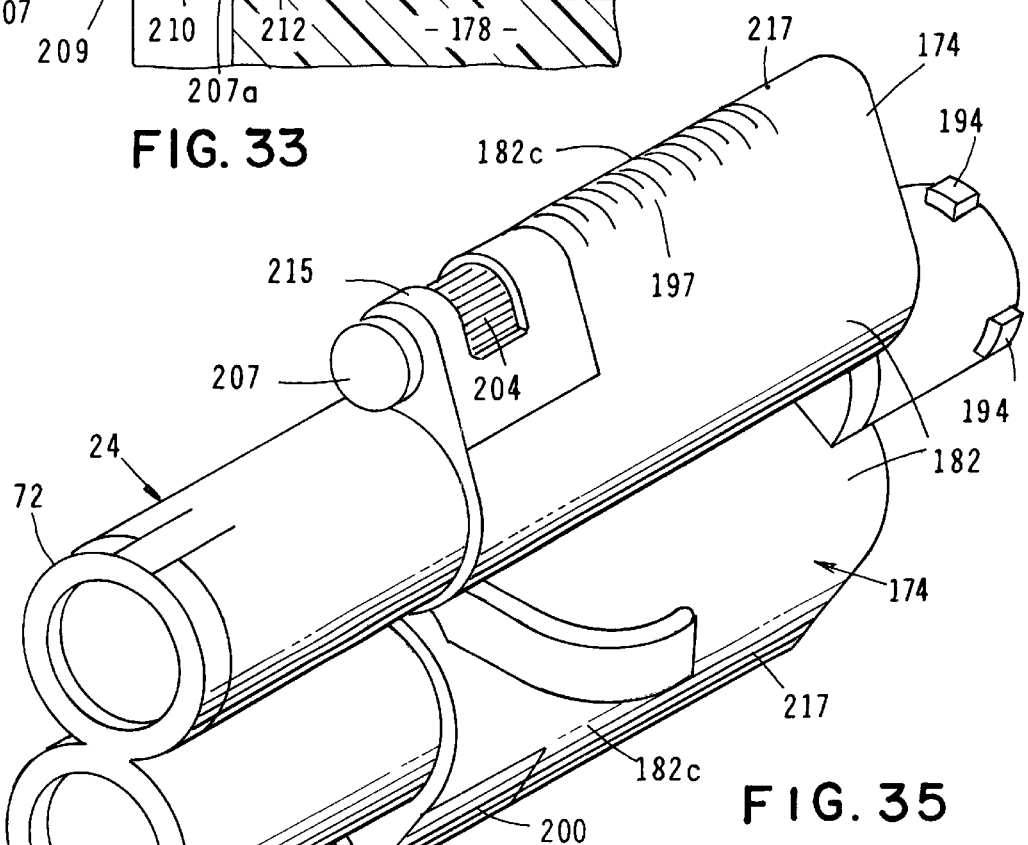
FIG. 35 is a generally perspective view of still another form of adapter fill assembly of the present invention.

Turning next to FIGS. 35 through 46, still another form of the second, or adapter fill means of the invention is there shown and generally designated by the numeral 215. This fill means, which is also used to fill reservoir 34, is similar in many respects to the embodiment shown in FIGS. 24, 25, and 26 and like numerals are used to identify like components. Referring particularly to FIG. 35, it is to be noted that fill means 215 here comprises a pair of interconnected, back-to-back fill assemblies 217, each of which is comparable in construction to the earlier described adapter fill means 170. As before, fill means 215 is specially designed to be sealably mated with fill port assembly 52 of the fluid delivery component 20. As illustrated in FIG. 35, each of the back-to-back fill assemblies 217 include a fill assembly 24 which is identical to that previously described and an adapter assembly 174 which is substantially identical to that previously described and telescopically accepts the container subassembly 60 of the fill assembly 24.

Figure 36:
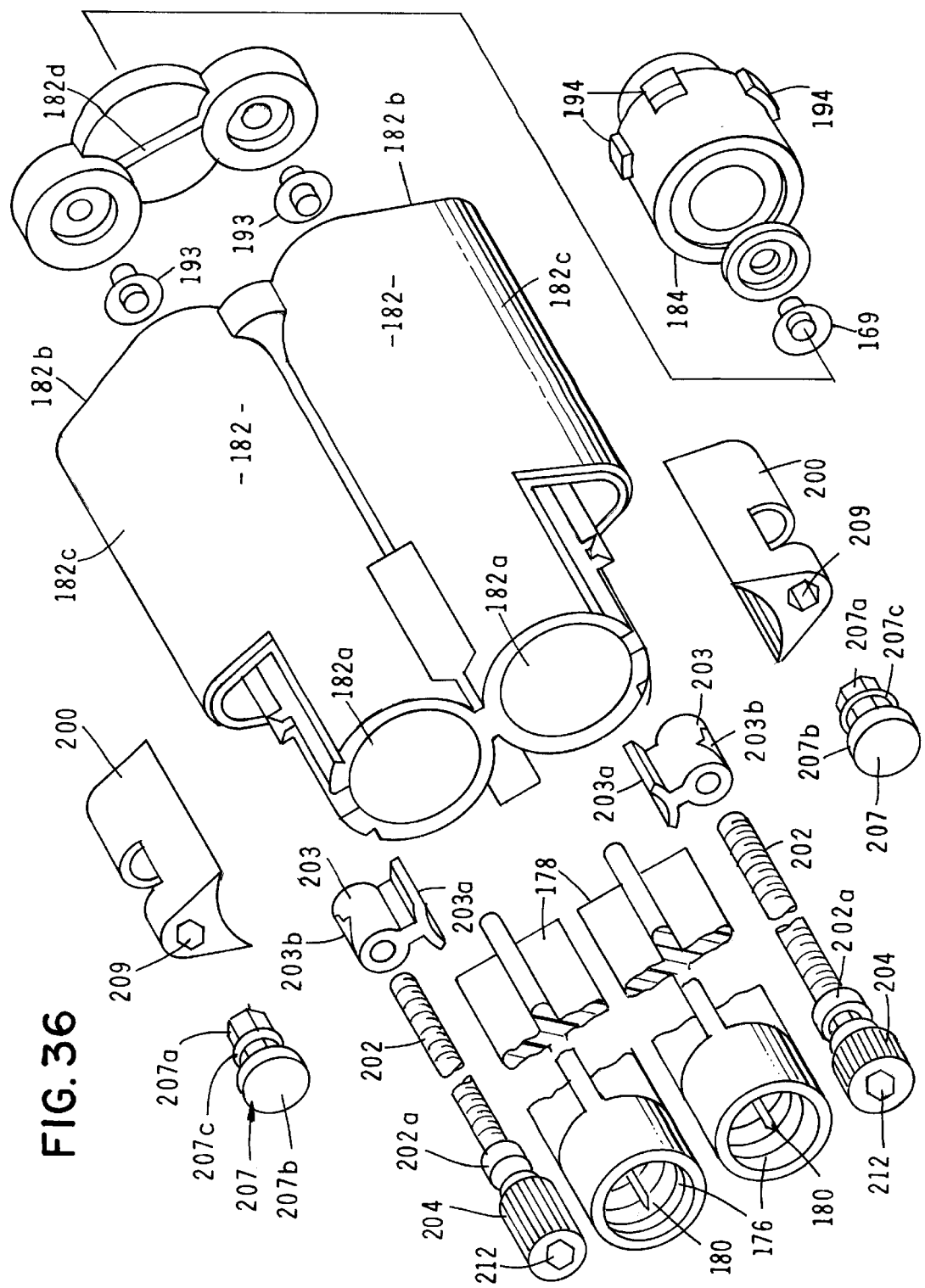
FIG. 36 is a generally perspective, exploded view of the fill assembly shown in FIG. 35.
Figure 37:
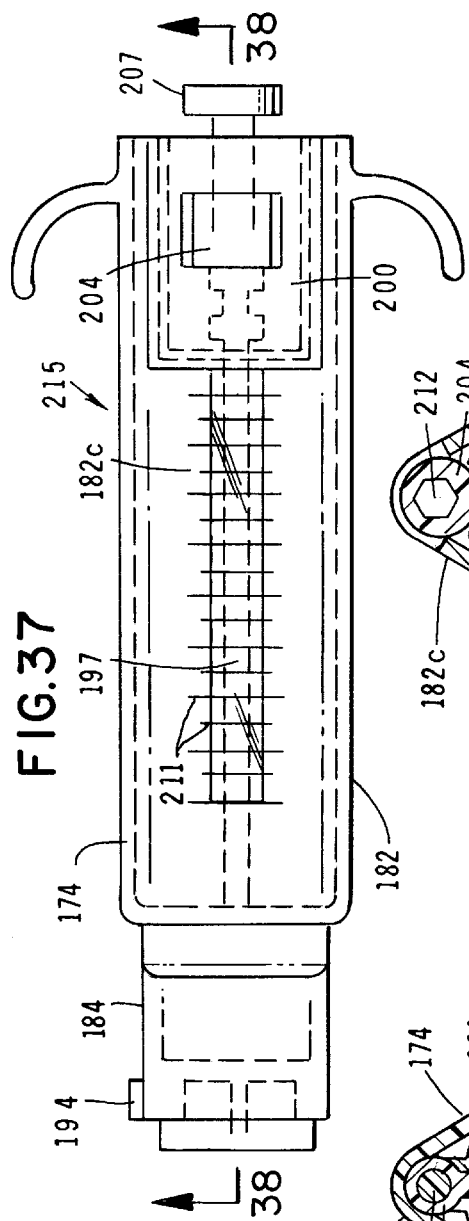
FIG. 37 is a top plan view of the adapter fill assembly shown in FIG. 35.
Figure 39:
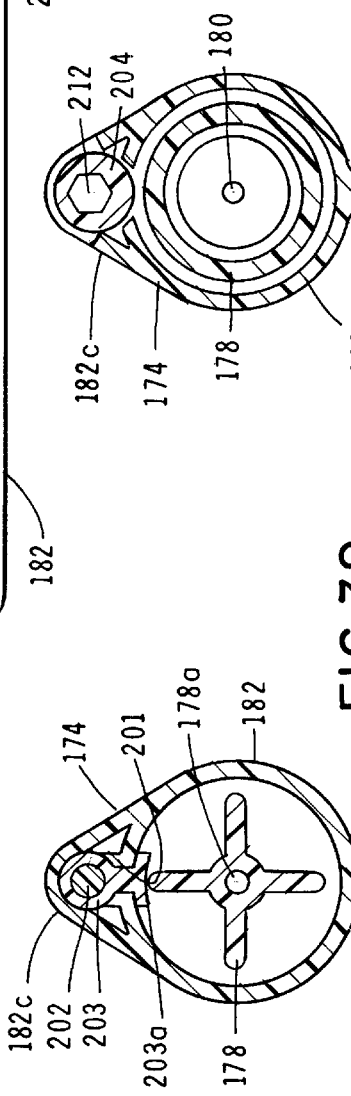
FIG. 39 is a cross-sectional view taken along lines 39—39 of FIG. 38.
Figure 40:
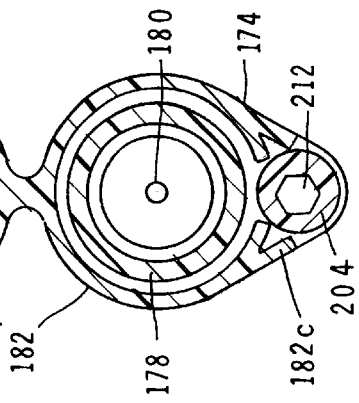
FIG. 40 is a cross-sectional view taken along lines 40—40 of FIG. 38.
Figure 41:
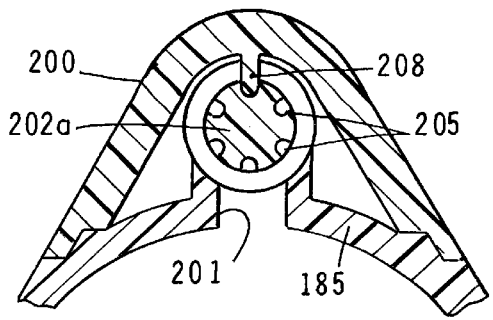
FIG. 41 is an enlarged cross-sectional view taken along lines 41—41 of FIG. 38.
Figure 42:
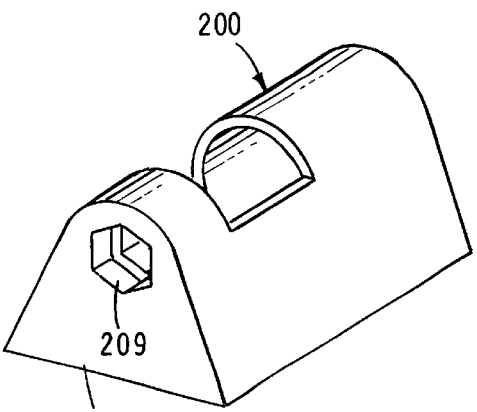
FIG. 42 is a generally perspective top view of the indicator housing of the form of the invention shown in FIG. 35.
Figure 45:
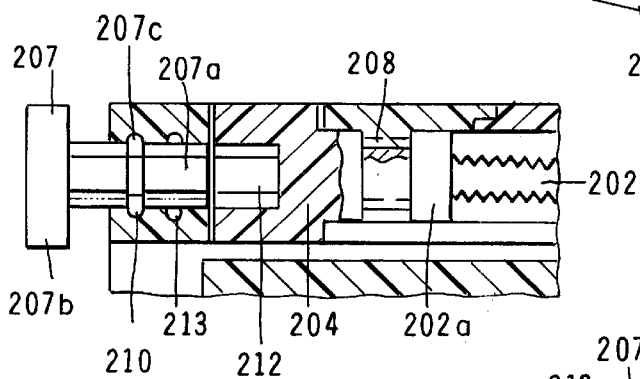
FIG. 45 is an enlarged, fragmentary, cross-sectional view of the locking means portion of the fill adapter shown in FIG. 35.
Figure 46:
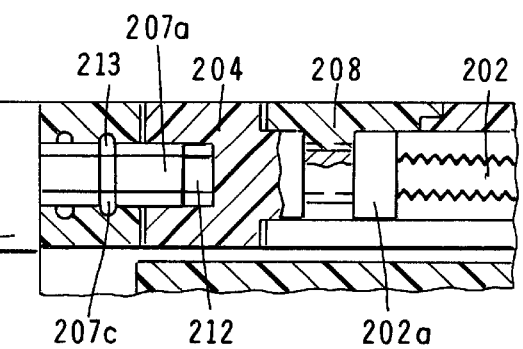
FIG. 46 is a fragmentary, cross-sectional view similar to FIG. 45, but showing the locking member in a locked position.
Figure 43:
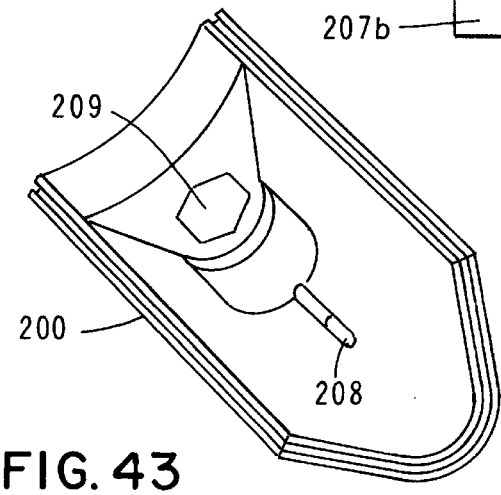
FIG. 43 is a generally perspective bottom view of the indicator housing shown in FIG. 42.
Figure 44:
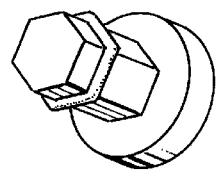
FIG. 44 is a generally perspective view of one form of the locking means of this latest form of the invention.

As before, threads 69 provided on plunger 68 of the container subassembly 60 (FIG. 16A) can be threadably connected to threads 176 provided on pusher member 178 of each of the adapter assemblies 174 (see FIG. 36). Pusher member 178 also includes a cannula 180 which is constructed and arranged to pierce the central wall 68a of plunger 68 when the container subassembly 60 is mated with the adapter assembly 174 in the manner previously described. As before, cannula 180 comprises a part of the adapter flow control means of the adapter assembly for controlling fluid flow toward reservoir 34.

Referring particularly to FIGS. 36 and 38, it can be seen that each of the back-to-back adapter subassemblies 174 is of the general construction previously described in connection with the embodiment of FIGS. 24 through 34 save for a common integral housing and each comprises a generally cylindrically shaped hollow container receiving housing 182 having a first open end 182a and a second closed end 182b. Container subassembly 60 is telescopically receivable within open end 182a of housing 182 so that the container 60a thereof can be moved from a first extended position shown in FIGS. 24A and 35 to a second, advanced position wherein container 60a is at least partially encapsulated within housing 182.

Also forming a part of the adapter fill means of this latest form of the invention is a connector means or cap assembly 184 (FIG. 35) which is connected to end portions 182b of housing 182 in the manner shown in FIG. 38. As before, cap assembly 184 includes a generally cylindrical exterior wall 186, the interior surface of which forms a chamber 188 into which a cannula 190 extends (FIG. 38). To interconnect fill means 215 with the fluid delivery component, the barrel-like portion of closure cap 184 is sealably mated with fill port 52 formed in base 42. As the barrel-like portion enters the lower portion of the fill port, the circumferentially spaced tabs 194 of closure cap 184 (see FIGS. 35 and 38) are received within circumferentially spaced tab receiving slots 146 formed in the fill port (FIG. 1). As before, cap 184 is provided with an elastomeric O-ring 195 so that an inward pressure exerted on the adapter assembly will effect a secure interconnection and sterile coupling of the fill means with the fill port 52. As the fill means 215 is mated with the delivery component, cannula 190 of closure cap 184 will pierce a pierceable septum 148 which is mounted within fill port 52. Provided between cannula 190 and each of the container subassemblies 60 are flow control means, shown here as a pair of check valves 193 which, along with check valve 169, control fluid flow toward cannula 190. The chambers that house check valves 193 communicate with the chamber that houses check valve 169 via flow passageways 182d. Similarly the chamber that houses check valve 169 communicates with cannula 190 via a passageway 169a.

As best seen by referring to FIGS. 36 through 40, each container receiving housing 182 includes an upper, curved portion and 182c which is provided with an elongated viewing window 197. Connected to each container receiving housing 182 and forming a continuation of upper portion 182c thereof is an indicator housing 200 that houses a portion of the volume control means of this latest form of the invention for controlling the volume of fluid to be introduced into reservoir 34. This volume control means is identical to that previously described and operates in an identical manner.

As in the earlier described embodiment, the position of stop member 203 of the volume control means within each of the hollow housings 182 will control the extent of travel of the container subassembly 60 of the fill means 24 into that housing and thusly will control the amount of fluid contained within the particular container subassembly 60 that will be introduced into reservoir 34 of the fluid delivery component 20.

This latest embodiment, like the earlier described embodiment, also comprises locking means for locking the stop members 203 in a selected position within each of the hollow housings 182. This locking means is also identical in construction and operation to that described in connection with the previously discussed embodiment of the invention. As before, when the locking means of a selected one of the adapter subassemblies 174 is moved into the second, locking position shown in FIG. 46, shaft portion 207a of that locking means extends into a generally hexagon-shaped opening 212 formed in the outboard end of shaft 202 of that locking means and rib-like portion 207c seats within second circumferentially extending grooves 213 that are formed within opening 209 of the adapter subassembly. When the locking means is in the second locked position and shaft portion 207a is received within the opening 212, shaft 202 is securely locked against further rotation by rotation of the control knob 204. Accordingly, as long as the locking means is in the locked position shown in FIG. 46, the position of the locking member 203 within the selected housing 182 cannot be changed and the volume of fluid to be introduced into the reservoir of the fluid delivery component from the container of that subassembly will remain unchanged.

With the novel construction of this latest, dual-container subassembly embodiment, selected fluids in selected, controlled volumes can be separately or simultaneously introduced into the fluid reservoir of the fluid delivery component.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A device for use in infusing medicinal fluid into a patient at a controlled rate comprising:
    (a) a fluid dispenser including:
        (i) a base having receiving chamber and an inlet port;
        (ii) a stored energy means for forming, in conjunction with said base, a fluid reservoir having an inlet in communication with said chamber and an outlet, said stored energy means comprising at least one distendable member superimposed over said base, said member being distendable as a result of pressure imparted by the fluids to be infused to establish internal stresses, said stresses tending to move said member toward a less distended configuration;
    (b) fill means interconnected with said receiving chamber of said base for filling said reservoir, said fill means comprising:
        (i) a container subassembly receivable within said receiving chamber, said container subassembly including:
            a. a container having a fluid chamber having first and second ends;
            b. displacement means movable relative to said fluid chamber for dispensing fluid from said chamber; and
            c. closure means for closing said second end of said fluid chamber of said container and connector means for interconnecting said fluid chamber of said container with a source of fluid.
    (c) second fill means interconnected with said inlet port of said base for filling said reservoir.

2. The delivery device as defined in claim 1 in which said connector means includes a housing, a pierceable septum and a closure panel hingedly connected to said housing for gaining access to said pierceable septum.

3. The delivery device as defined in claim 1 in which said connector means includes a luer connector connected to said container.

4. The device as defined in claim 1 further including infusion means connected to said base and being in fluid communication with said fluid reservoir for infusing medicinal fluids into a patient.

5. The device as defined in claim 1 in which said second fill means comprises a container assembly including a container having a fluid chamber and displacement means movable within said fluid chamber and an adapter assembly comprising a hollow housing having an outlet in communication with said inlet of said fluid reservoir and also having a barrel portion receivable within said inlet port of said base to connect said adapter assembly to said base, said container being telescopically receivable in said housing.

6. The device as defined in claim 5, in which said adapter assembly comprises pusher means for engagement with said displacement means of said container assembly to move said displacement means within said fluid chamber to urge fluid flow toward said fluid reservoir.

7. The device as defined in claim 6 in which said pusher means comprises a pusher member disposed within said hollow housing of said adapter subassembly.

8. The device defined in claim 6 in which said adapter assembly further comprises volume control means for controlling the volume of fluid introduced into said reservoir.

9. The device as defined in claim 8 in which said hollow housing of said adapter assembly is provided with an elongated track and in which said volume control means comprises a stop member assembly slidably movable relative to said track from a first position to a second position.

10. The device as defined in claim 9 in which said hollow housing of said adapter assembly is provided with volume indicating indicia disposed proximate said elongated track.

11. The device as defined in claim 9 in which said stop member assembly comprises a push button slidably receivable within said track of said indicator housing.

12. The device as defined in claim 11 further including locking means for locking said push button in position.

13. The device as defined in claim 11 in which said fluid dispenser further includes fluid actuated indicator means for visually indicating fluid flow from said fluid reservoir.

14. A device for use in infusing medicinal fluid into a patient at a controlled rate comprising:
(a) a fluid dispenser including:
  (i) a base having an inlet port;
  (ii) a stored energy means for forming, in conjunction with said base a fluid reservoir having an inlet in communication with said inlet port and an outlet, said stored energy means comprising at least one distendable member superimposed over said base, said member being distendable as a result of pressure imparted by the fluids to be infused to establish internal stresses, said stresses tending to move said member toward a less distended configuration; and
  (iii) an outlet port in communication with said outlet of said fluid reservoir for dispensing fluids from the device;
(b) an adapter fill assembly interconnectable with said inlet port of said base for filling said fluid reservoir thereof, said adapter fill assembly comprising:
  (i) a container subassembly including a container having a fluid chamber and displacement means movable within said fluid chamber; and
  (ii) an adapter assembly comprising:
    a. a container-receiving housing having an elongated track, an outlet in communication with said inlet of said fluid reservoir and a barrel portion connected to said container receiving housing, said barrel portion being receivable within said inlet port of said base of said fluid dispenser to connect said adapter assembly to said base, said container being telescopically receivable in said container-receiving housing; and
    b. volume control means for controlling the volume of fluid to be introduced into said fluid reservoir, said volume control means comprising a stop member slidably movable along said elongated track of said container-receiving housing from a first position to a second position, said stop member including a portion engageable by said container of said container subassembly.

15. The device as defined in claim 14 in which said adapter assembly further comprises locking means for locking said stop member in position.

16. The device as defined in claim 14 in which said adapter assembly further comprises operating means for moving said stop member along said elongated track.

17. The device as defined in claim 14 in which said inlet port of said base includes a pierceable septum and in which said adapter assembly further comprises a cannula for piercing said pierceable septum.

18. The device as defined in claim 14 in which said adapter fill assembly further includes a second adapter assembly having a container receiving housing for receiving a container.

19. The device as defined in claim 14 in which said base includes a receiving chamber and in which said device further includes a fill means receivable within said receiving chamber of said base for filling said reservoir, said fill means comprising:
(a) a container subassembly receivable within said receiving chamber, said container subassembly including:
  (i) a container having a fluid chamber having first and second ends;
  (ii) displacement means movable relative to said fluid chamber for dispensing fluid from said chamber; and
  (iii) closure means for closing said second end of said fluid chamber of said container, said closure means including a closure subassembly connected to said second end of said container, said closure subassembly comprising a housing, a closure panel hingedly connected to said housing and connector means for interconnecting said fluid chamber of said container with a source of fluid.

20. A device for use in infusing medicinal fluid into a patient at a controlled rate comprising:
(a) a fluid dispenser including:
  (i) a base having receiving chamber and an inlet port;
  (ii) a stored energy means for forming, in conjunction with said base a fluid reservoir having an inlet in communication with said chamber and an outlet, said stored energy means comprising at least one distendable member superimposed over said base, said member being distendable as a result of pressure imparted by the fluids to be infused to establish internal stresses, said stresses tending to move said member toward a less distended configuration; and
  (iii) an outlet port in communication with said outlet of said fluid reservoir for dispensing fluids from the device;

(iv) fluid actuated indicator means for visually indicating fluid flow from said reservoir; and
(b) an adapter fill means interconnectable with said inlet port of said base for filling said fluid reservoir thereof, said adapter fill means comprising:
  (i) a container subassembly including a container having a fluid chamber and displacement means movable within said fluid chamber;
  (ii) a first adapter assembly comprising:
    a. a container-receiving housing having an elongated track, an outlet in communication with said inlet of said fluid reservoir and a barrel portion receivable within said inlet port of said base of said fluid dispenser to connect said adapter assembly to said base, said container being telescopically receivable within said housing; and
    b. volume control means for controlling the volume of fluid to be introduced into said fluid reservoir of said fluid dispenser, said volume control means comprising a stop member assembly movable relative to said elongated tracks from a first position to a second position, for engagement by said container of said container subassembly; and
  (iii) locking means for locking said stop member assembly in position relative to said elongated track;
(c) a fill assembly receivable within said receiving chamber of said base, said fill assembly including a container assembly comprising:
  (i) a container having a fluid chamber having first and second ends;
  (ii) displacement means movable relative to said fluid chamber for dispensing fluid from said chamber; and
  (iii) closure means for closing said second end of said fluid chamber of said container, said closure means including a closure subassembly connected to said second end of said container, said closure subassembly comprising a housing.

21. The device as defined in claim 20 in which said closure means comprises a closure panel hingedly connected to said housing and connector means for interconnecting said fluid chamber of said container with a source of fluid.

22. The device as defined in claim 20 further including a second adapter assembly operably associated with said first adapter assembly.

23. The device as defined in claim 20 in which said container receiving housing of said first adapter assembly includes a plurality of longitudinally spaced apart locking teeth, in which said stop member assembly comprises a push button, and in which said locking means comprises a pair of arms connected to said push button; each of said arms having tabs engageable with said locking teeth.

24. The device as defined in claim 23 in which said stop member assembly comprises a stop member and in which said volume control means comprises a threaded shaft connected to said stop member.

25. The device as defined in claim 23 in which said volume control means further comprises operating means for imparting rotation to said threaded shaft.

26. The device as defined in claim 24 further including locking means for locking said threaded shaft against rotation.

* * * * *